(12) United States Patent
Li et al.

(10) Patent No.: US 10,023,831 B2
(45) Date of Patent: Jul. 17, 2018

(54) GAS DELIVERY DEVICES AND ASSOCIATED SYSTEMS AND METHODS

(71) Applicants: Biogen Idec MA Inc., Cambridge, MA (US); North Carolina State University, Raleigh, NC (US)

(72) Inventors: Fanxing Li, Cary, NC (US); Weiwei Hu, Cary, NC (US); Yang Liu, Raleigh, NC (US); Kelly Wiltberger, Durham, NC (US); Haofan Peng, Cary, NC (US); Rachel Ferguson, Morrisville, NC (US)

(73) Assignees: Biogen MA Inc., Cambridge, MA (US); North Carolina State University, Raleigh, NC (US)

( * ) Notice: Subject to any disclaimer, the term of this patent is extended or adjusted under 35 U.S.C. 154(b) by 0 days.

(21) Appl. No.: 15/126,332

(22) PCT Filed: Mar. 17, 2015

(86) PCT No.: PCT/US2015/021009
§ 371 (c)(1),
(2) Date: Sep. 15, 2016

(87) PCT Pub. No.: WO2015/142881
PCT Pub. Date: Sep. 24, 2015

(65) Prior Publication Data
US 2017/0081623 A1 Mar. 23, 2017

Related U.S. Application Data

(60) Provisional application No. 61/954,496, filed on Mar. 17, 2014.

(51) Int. Cl.
*B01F 3/04* (2006.01)
*C12M 1/107* (2006.01)

(52) U.S. Cl.
CPC ......... *C12M 21/04* (2013.01); *B01F 3/04248* (2013.01); *B01F 3/04262* (2013.01);
(Continued)

(58) Field of Classification Search
CPC .... B01F 3/04; B01F 3/04106; B01F 3/04241; B01F 3/04248; C02F 1/72
(Continued)

(56) References Cited

U.S. PATENT DOCUMENTS 2,815,943 A 12/1957 Lamb
3,644,231 A 2/1972 Marilyn et al.
(Continued)

FOREIGN PATENT DOCUMENTS

JP H03-19600 U 2/1991
WO WO 2012/081481 A1 6/2012

OTHER PUBLICATIONS

Akagi et al., Liquid weeping accompanied by bubble formation at submerged orifices. Ind. Eng. Chem. Res. 1987;26(8):1546-50.
(Continued)

*Primary Examiner* — Robert A Hopkins
(74) *Attorney, Agent, or Firm* — Wolf, Greenfield & Sacks, P.C.

(57) ABSTRACT

Systems, devices, and methods for the delivery of gas bubbles to liquids are generally described. The devices can include a primary conduit comprising a plurality of openings fluidically connecting an internal flow pathway of the primary conduit to an environment outside the primary conduit. The devices may also include, in some instances, a secondary conduit located at least partially within the primary conduit, the secondary conduit configured to redistribute the pressure of the gas delivered to the openings of the primary conduit, and comprising a plurality of openings fluidically connecting an internal flow pathway of the secondary con-
(Continued)

duit to a portion of the internal flow pathway of the primary conduit outside the secondary conduit. Certain of the gas delivery systems and methods described herein are capable of delivering gas at relatively uniform linear flow velocities across multiple gas outlet openings. Certain embodiments are related to inventive configurations (e.g., spacings and/or sizing) of gas outlet openings in one or more conduits of the gas delivery device (e.g., the primary conduit and/or, when present, the secondary conduit). In addition, some embodiments are related to inventive arrangements for joining a gas delivery device to a vessel, which may be part of for example, a reactor such as a bioreactor. Certain embodiments are related to the orientation of the gas delivery device and/or its components (e.g., during operation).

20 Claims, 17 Drawing Sheets

(52) U.S. Cl.
CPC ............ *B01F 2003/04319* (2013.01); *B01F 2003/04354* (2013.01); *B01F 2215/0073* (2013.01); *B01F 2215/0431* (2013.01); *B01F 2215/0481* (2013.01)

(58) Field of Classification Search
USPC ...................................... 261/121.1
See application file for complete search history.

(56) References Cited

U.S. PATENT DOCUMENTS

| | | | |
|---|---|---|---|
| 3,911,064 | A | 10/1975 | McWhirter et al. |
| 3,970,731 | A | 7/1976 | Oksman |
| 4,048,072 | A | 9/1977 | McCullough |
| 5,078,922 | A | 1/1992 | Collins et al. |
| 7,318,901 | B2 * | 1/2008 | Naess ............... A01K 63/042 210/220 |
| 2011/0312087 | A1 | 12/2011 | Khan | |

OTHER PUBLICATIONS

Cherry et al., Cell death in the thin films of bursting bubbles. Biotechnol Prog. Jan.-Feb. 1992;8(1):11-8.
Handa et al., On the evaluation of gas-liquid interfacial effects on hybridoma viability in bubble column bioreactors. Dev Biol Stand. 1987;66:241-53.
Liu et al., Effects of bubble-liquid two-phase turbulent hydrodynamics on cell damage in sparged bioreactor. Biotechnol Prog. Jan.-Feb. 2014;30(1):48-58.
Michaels et al., Analysis of cell-to-bubble attachment in sparged bioreactors in the presence of cell-protecting additives. Biotechnol Bioeng. Aug. 20, 1995;47(4):407-19.
Thorat et al., Design of Sieve Plate Spargers for Bubble Columns: Role of Weeping. Chemical Engineering & Technology. Aug. 2001;24(8):815-28.
Invitation to Pay Additional Fees for PCT/US2015/021009 dated Jun. 25, 2015.
International Search Report and Written Opinion for PCT/US2015/021009 dated Aug. 31, 2015.
International Preliminary Report on Patentability for PCT/US2015/021009 dated Sep. 29, 2016.
Barbosa et al., Hydrodynamic stress and lethal events in sparged microalgae cultures. Biotechnol Bioeng. Jul. 5, 2003;83(1):112-20.
Barbosa et al., Overcoming shear stress of microalgae cultures in sparged photobioreactors. Biotechnol Bioeng. Jan. 5, 2004;85(1):78-85.
Chisti, Animal-cell damage in sparged bioreactors. Tibtech. Oct. 2000;18:420-32.
Handa-Corrigan et al., Effect of gas-liquid interfaces on the growth of suspended mammalian cells: mechanisms of cell damage by bubbles. Enzyme Microb. Technol. Apr. 1989;11:230-5.
Jöbses et al., Lethal events during gas sparging in animal cell culture. Biotechnol Bioeng. Mar. 5, 1991;37(5):484-90.
Kulkarni, Design of a Pipe/Ring Type of Sparger for a Bubble Column Reactor. Chem. Eng. Technol. 2010;33(6):1015-22.
Liu et al., Effects of bubble-liquid two-phase turbulent hydrodynamics on cell damage in sparged bioreactor. 245$^{th}$ ACS National Meeting. New Orleans, Louisiana. Apr. 10, 2013. Abstract.
Liu et al., Sparger design for improved bubble-liquid hydrodynamics in bioreactors. 249$^{th}$ ACS National Meeting. Denver, Colorado. Mar. 26, 2015. Abstract.
Michaels et al., Sparging and agitation-induced injury of cultured animals cells: Do cell-to-bubble interactions in the bulk liquid injure cells? Biotechnol Bioeng. Aug. 20, 1996;51(4):399-409.
Papoutsakis, Fluid-mechanical damage of animal cells in bioreactors. Tibtech. Dec. 1991;9:427-37.
Stamper et al., Bioreactor Operational Excellence: Best Practices from Scale-up to Control. Pharmaceutical Manufacturing. Apr. 2, 2009. Last accessed on Mar. 6, 2016 from <http://www.pharmamanufactruing.com/articles/2009/045/?show=all>. 12 pages.
Trinh et al., Quantification of damage to suspended insect cells as a result of bubble rupture. Biotechnol Bioeng. Jan. 5, 1994;43(1):37-45.
Zhu et al., NS0 cell damage by high gas velocity sparging in protein-free and cholesterol-free cultures. Biotechnol Bioeng. Nov. 1, 2008;101(4):751-60. doi: 10.1002/bit.21950.

* cited by examiner

GAS DELIVERY DEVICES AND ASSOCIATED SYSTEMS AND METHODS

RELATED APPLICATIONS

This application is a U.S. National Stage patent application based on International Application PCT/US2015/021009, filed Mar. 17, 2015, and entitled "Gas Delivery Devices and Associated Systems and Methods", which claims priority under 35 U.S.C. § 119(e) to U.S. Provisional Patent Application Ser. No. 61/954,496, filed Mar. 17, 2014, and entitled "Gas Delivery Devices and Associated Systems and Methods," each of which is incorporated herein by reference in its entirety for all purposes.

TECHNICAL FIELD

Systems, devices, and methods for the delivery of gas bubbles to liquids are generally described.

BACKGROUND

Gas sparging is a process by which gas is bubbled through a liquid medium. Typically, gas sparging is performed by transporting the gas through a tube comprising a plurality of nozzles; upon exiting the nozzles, the gas forms bubbles, which are subsequently transported through the liquid medium in which the tube is positioned.

Gas sparging is a commonly used strategy for the submerged culture of microorganisms, including aerobic microorganisms. In some such cases, gas sparging may be used to maintain desirable liquid levels of dissolved oxygen, carbon dioxide, and/or other gases required by the microorganisms that are being grown. While transporting such gases to microorganisms may be essential for growth, bubble formation, movement, and rupture can exert significant stress, potentially damaging the microorganisms. This can be especially problematic for sensitive species such as animal cells, microalgae, or certain bacteria.

Improved systems and methods for bubbling gas through liquid media in which cell death is reduced (or substantially eliminated) would be desirable.

SUMMARY

The delivery of gas bubbles to liquids, and associated systems and articles, are generally described. The subject matter of the present invention involves, in some cases, interrelated products, alternative solutions to a particular problem, and/or a plurality of different uses of one or more systems and/or articles.

Certain aspects relate to devices for producing bubbles of a gas within a liquid. In some embodiments, the device comprises a primary conduit comprising a plurality of openings fluidically connecting an internal flow pathway of the primary conduit to an environment outside the primary conduit; and a secondary conduit located at least partially within the primary conduit, the secondary conduit configured to redistribute the pressure of the gas delivered to the openings of the primary conduit, and comprising a plurality of openings fluidically connecting an internal flow pathway of the secondary conduit to a portion of the internal flow pathway of the primary conduit outside the secondary conduit.

Some embodiments relate to methods of producing bubbles of a gas within a liquid. In certain embodiments, the method comprises transporting gas through a gas inlet opening of a primary conduit comprising a plurality of primary conduit gas outlet openings fluidically connecting an internal flow pathway of the primary conduit to an environment outside the primary conduit, wherein a portion of the gas is transported through a gas inlet opening of a secondary conduit located at least partially within the primary conduit, and the portion of the gas is transported through gas outlet openings of the secondary conduit prior to being transported through gas outlet openings of the primary conduit such that the secondary conduit redistribute the pressure of the gas delivered to the gas outlet openings of the primary conduit.

In some embodiments, the method comprises transporting gas through a gas inlet opening of a primary conduit such that the gas is transported from an interior of the primary conduit to an environment within the liquid and outside the primary conduit via a plurality of gas outlet openings, wherein, for at least 80% of the gas outlet openings, gas is transported through the gas outlet opening at a linear velocity that is within 20% of the average of the linear velocities at which gas is transported through the gas outlet openings, for all average linear velocities of from about 0.1 m/s to about 40 m/s.

In certain embodiments, the method comprises transporting gas through a first gas inlet opening of a primary conduit such that the gas is transported from an interior of the primary conduit to an environment within the liquid and outside the primary conduit via a plurality of gas outlet openings, wherein, for at least 80% of the gas outlet openings, gas is transported through the gas outlet opening at a linear velocity that is within 20% of the average of the linear velocities at which gas is transported through the gas outlet openings, and the primary conduit does not include a second gas inlet opening.

Certain aspects relate to methods of operating a bioreactor. In some embodiments, the method comprises transporting gas through a gas inlet opening of a primary conduit positioned within a liquid contained within the bioreactor such that the gas is transported from an interior of the primary conduit to an environment within the liquid and outside the primary conduit via a plurality of gas outlet openings; wherein, for at least 80% of the gas outlet openings, gas is transported through the gas outlet opening at a linear velocity that is within 20% of the average of the linear velocities at which gas is transported through the gas outlet openings.

Certain embodiments are related to inventive configurations (e.g., spacings and/or sizing) of gas outlet openings in one or more conduits of the gas delivery device (e.g., the primary conduit and/or, when present, the secondary conduit). In addition, some embodiments are related to inventive arrangements for joining a gas delivery device is to a vessel, which may be part of, for example, a reactor such as a bioreactor. Certain embodiments are related to the orientation of the gas delivery device and/or its components (e.g., during operation).

In certain embodiments, a device for producing bubbles of a gas within a liquid is described. In some embodiments, the device comprises a conduit comprising a plurality of openings fluidically connecting an internal flow pathway of the conduit to an environment outside the conduit, wherein an average of cross-sectional diameters of the openings is less than about 2.5 mm, and an average of nearest neighbor distances between the openings of the conduit is at least about 2 mm.

In some embodiments, the device for producing bubbles of a gas within a liquid, comprises an elongated vessel connection portion configured to be connected to a vessel, the elongated vessel connection portion comprising a longitudinal axis; and a gas delivery portion comprising a plurality of openings fluidically connecting an internal flow pathway of the gas delivery portion to an environment outside the gas delivery portion, wherein the longitudinal axis of the vessel connection portion is angled relative to the gas delivery portion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The delivery of gas to liquids, and associated systems and articles, are generally described. Certain embodiments relate to systems and articles that can be used to deliver gas through multiple outlets of a gas delivery device at relatively consistent linear velocities. The delivery of gas in such a controlled manner can be helpful in reducing or substantially eliminating cell death in bioreactors in which gas delivery is used to perform cell culture and/or other biochemical reactions.

Without being bound by any particular theory, it is believed that the rupture of bubbles near the gas-liquid interface of gas delivery devices (such as spargers) is an important contributing factor to cell death within bioreactors in which gas bubble delivery is employed. It is believed that significant cell damage can occur when linear gas velocities at the outlets of the gas delivery device are relatively high (e.g., higher than 30 m/s). It is further believed that relatively high turbulent energy dissipation rates, normal and shear stresses, turbulent kinetic energies, and stress-induced-turbulent-energy-production rates—all of which may contribute to cell damage and/or death—generally increase with increasing gas velocities at the outlets of the gas delivery device. It is also believed that large linear gas velocities generally result in the production of relatively small gas bubbles within the liquid medium, which can also lead to cell damage and/or death.

One could potentially avoid cell damage and/or death by lowering the overall flow rate of gas through the openings of the gas delivery device. However, lowering gas flow rate can lead to a phenomenon commonly referred to as "weeping," in which certain outlet openings expel gas only at very low linear velocities (or, in some cases, at linear velocities of zero). Weeping within the gas delivery device reduces the overall efficiency with which gas is introduced into the liquid medium. In addition, weeping can lead to cell growth and/or accumulation at or near the outlet openings of the gas delivery device, which can clog the openings, increase linear gas velocities, and necessitate undesirable downtime (e.g., for cleaning the gas delivery device).

Alternatively, and as described in more detail below, one can reduce cell damage and/or death and weeping by configuring the gas delivery device to deliver gas at relatively constant linear velocities across the openings of the gas delivery device. By introducing gas at relatively constant linear velocities across the device, one can ensure that few or none of the individual openings expel gas too quickly (thereby causing cell damage and/or death) or too slowly (thereby causing weeping).

Figure 1A:
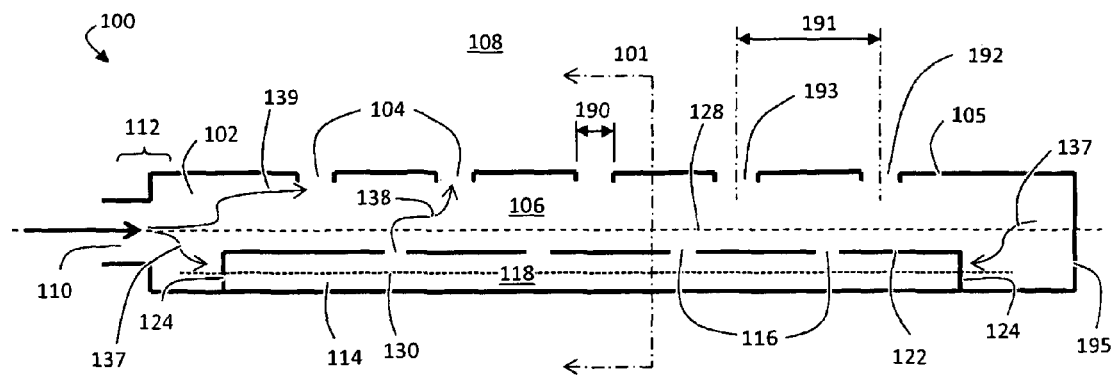
FIGS. 1A-1B are cross-sectional schematic illustrations of a device for producing bubbles of gas within a liquid, according to one set of embodiments.
Figure 1B:
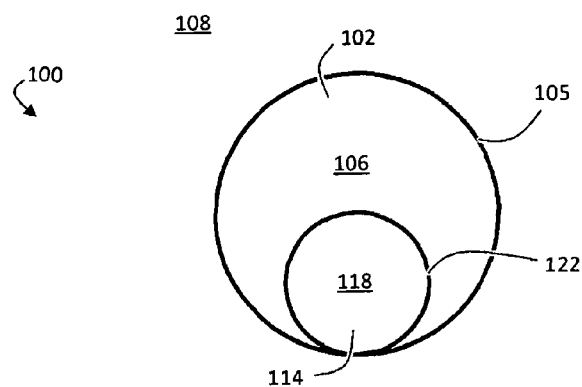

Accordingly, certain embodiments of the instant disclosure relate to devices for producing bubbles of gas within a liquid which can be used to deliver the gas at relatively uniform linear velocities from opening to opening. FIG. 1A is a schematic cross-sectional illustration of device 100 for producing bubbles of a gas within a liquid. FIG. 1B is a cross-sectional schematic illustration of the device of FIG. 1A, with the cross-section taken perpendicular to the view illustrated in FIG. 1A and along section 101.

In FIGS. 1A-1B, device 100 comprises primary conduit 102. Primary conduit 102 may be in the form of, for example, a tube. Primary conduit 102 comprises a plurality of openings 104 fluidically connecting internal flow pathway 106 of primary conduit 102 to environment 108 outside primary conduit 102. As described in more detail below, during operation of device 100, gas may be transported from internal flow pathway 106 of primary conduit 102 to environment 108 by establishing a pressure drop across openings 104 such that the gas is transported through the openings.

Openings 104 of primary conduit 102 can be located, for example, in the wall 105 of primary conduit 102. The openings can be formed using any of a variety of methods known to those of ordinary skill in the art. For example, in some embodiments, the openings are drilled or otherwise formed into a wall of the primary conduit after the primary conduit has been formed. In certain embodiments, the openings can be formed at the same time as the wall of the primary conduit (e.g., by molding the wall of the primary conduit such that it includes holes). The primary conduit can be configured to include any number of openings, including openings of a variety of sizes and shapes.

Primary conduit 102 also comprises gas inlet opening 110. The gas inlet opening can be located at or near an end of the primary conduit. For example, in FIG. 1A, gas inlet opening 110 is located at end 112 of primary conduit 102. The gas inlet opening can be configured to receive gas from an external source. For example, in certain embodiments, the gas inlet opening of the primary conduit is fluidically connected to a source of gas. The external gas source can be pressurized and, when connected to the gas inlet opening, can establish a pressure drop across the gas inlet opening such that gas is transported through the gas inlet opening into the internal flow pathway of the primary conduit. The gas source may contain a gas suitable for use, for example, in cell culture and/or other biochemical reaction processes. In certain embodiments, the source may include oxygen gas, carbon dioxide gas, and/or any other gas one desires to introduce into the liquid environment external to the primary conduit. The gas source may be fluidically connected to a gas inlet opening of the primary conduit using any suitable attachment mechanism known to those of ordinary skill in the art including, but not limited to, friction-based fittings, pressure fittings, threaded fittings, or any other suitable mechanism.

In certain embodiments, primary conduit 102 does not include a second gas inlet opening. By using a single gas inlet opening, operation of the gas delivery device can be simplified, according to certain embodiments, relative to instances in which gas is fed to the primary conduit via a plurality of inlet openings. For example, in embodiments including only one gas inlet opening, a single connection of a gas source to the gas delivery device is sufficient to commence operation. In addition to providing for simplified operation, the elimination of multiple gas inlet connections can make the gas delivery device easier to clean and/or otherwise maintain. While the use of primary conduits having a single gas opening can provide for advantageous operation according to certain embodiments, the embodiments described herein are not limited to devices having a single gas inlet opening, and may also include devices in which multiple gas inlet openings are present in the primary conduit.

Referring back to FIG. 1A, during use, gas (e.g., from the gas source) can be transported into primary conduit 102 through gas inlet opening 110, along internal flow pathway 106, and out of the primary conduit via gas outlet openings 104. Primary conduit 102 can include any suitable number of gas outlet openings 104. In certain embodiments, the primary conduit comprises at least three, at least five, at least 10, at least 50, at least 100 (and/or, in certain embodiments, up to 1000, 10,000, or more) gas outlet openings connecting an internal flow pathway of the primary conduit to environment outside the primary conduit. While the openings illustrated in FIG. 1A are shown as extending from the external surface of primary conduit 102 to the internal surface of primary conduit 102 in a substantially linear fashion, other orientations could also be employed. In some embodiments, one or more gas outlet openings in the primary conduit can be formed of a porous medium.

In certain embodiments, the gas delivery system includes a secondary conduit, in addition to the primary conduit. For example, referring to FIG. 1A, gas delivery device 100 comprises secondary conduit 114. Secondary conduit can comprise a plurality of openings fluidically connecting an internal flow pathway of the secondary conduit to a portion of the internal flow pathway of the primary conduit outside the secondary conduit. For example, referring back to FIG. 1A, secondary conduit 114 comprises openings 116, which fluidically connect internal flow pathway 118 of secondary conduit 114 to a portion of internal flow pathway 106 of primary conduit 102 that is outside the secondary conduit. While the figures illustrate a single interior conduit (secondary conduit 114), it should be noted that additional interior conduits could be employed, according to certain embodiments.

The openings of the secondary conduit may be located, in certain embodiments, in a wall of the secondary conduit. For example, in FIG. 1A, openings 116 are located in wall 122 of secondary conduit 114. The openings in the secondary conduit may be formed using a number of suitable techniques, as described in more detail below.

The secondary conduit can include one or more gas inlet openings, through which gas may be transported into the secondary conduit. For example, in FIG. 1A, secondary conduit 114 comprises gas inlet openings 124. The gas inlet opening of the secondary conduit can be located at or near an end of the secondary conduit. In FIG. 1A, gas inlet openings 124 are located at the ends of secondary conduit 114. In some embodiments, the secondary conduit does not include a second gas inlet opening.

The secondary conduit can include any suitable number of gas outlet openings. In certain embodiments, the secondary conduit comprises at least three, at least five, at least 10, at least 50, at least 100 (and/or, in certain embodiments, up to 1000, 10,000, or more) gas outlet openings connecting an internal flow pathway of the secondary conduit to an internal flow pathway of the primary conduit that is outside the secondary conduit. In certain embodiments, the ratio of the number of gas outlet openings in the secondary conduit to the number of gas outlet openings in the primary conduit can be between 1:1 and 75:1. The embodiments described herein are not limited to these specific ratios, and in some embodiments, the ratio of the number of gas outlet openings in the secondary conduit to the number of gas outlet openings in the primary conduit can be below 1:1 or above 75:1.

Secondary conduit 114 can be located at least partially within primary conduit 102. Any portion of the secondary conduit may be located within the primary conduit. For example, in certain embodiments, at least one gas outlet opening of the secondary conduit is located within the primary conduit. In some embodiments, at least one gas inlet opening of the secondary conduit is located within the primary conduit.

In certain embodiments, the entirety of the secondary conduit is located within the primary conduit. This may be accomplished, for example, by forming the entirety of the secondary conduit within the primary conduit, inserting the entirety of the secondary conduit into the primary conduit, or otherwise arranging the secondary conduit such that it is entirely contained within the internal flow pathway of the primary conduit. As one example, in FIGS. 1A-1B, the entirety of secondary conduit 114, including both gas inlet openings 124, is located within internal flow pathway 106 of primary conduit 102.

Figure 2A:
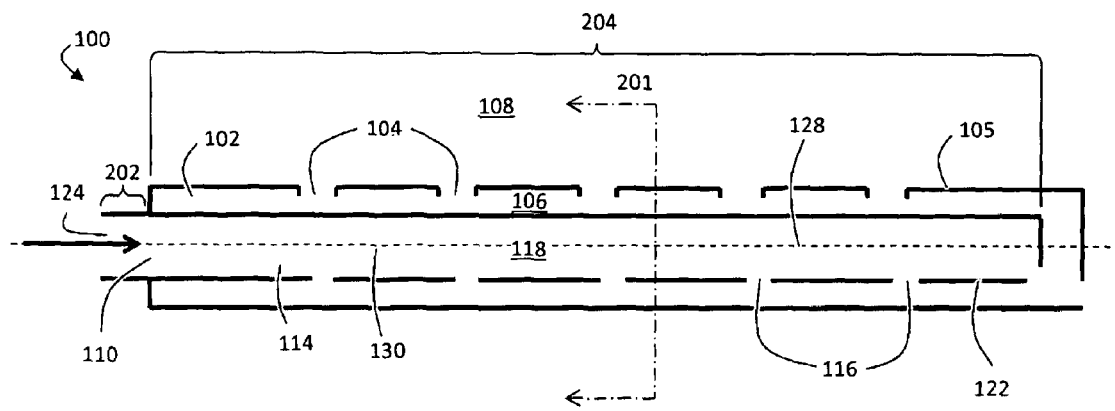
FIGS. 2A-2B are, according to certain embodiments, cross-sectional schematic illustrations of a device for producing bubbles of gas within a liquid.
Figure 2B:
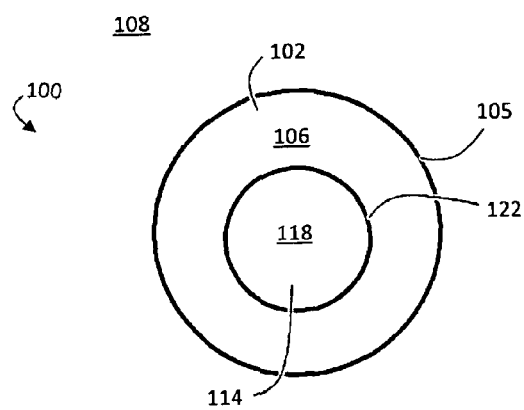

In some embodiments, only a portion of the secondary conduit is located within the primary conduit. This may be accomplished, for example, by forming only a portion of the secondary conduit within the primary conduit, inserting only a portion of the secondary conduit into the primary conduit, or otherwise arranging the secondary conduit such that only a portion of the secondary conduit is contained within the internal flow pathway of the primary conduit. One example of this arrangement is illustrated in FIGS. 2A-2B. (As with FIGS. 1A-1B, the cross-section illustrated in FIG. 2B is taken perpendicular to the view illustrated in FIG. 2A and along section 201.) In FIG. 2A, portion 202 of secondary conduit 114 is located outside primary conduit 102 while portion 204 of secondary conduit 114 is located inside primary conduit 102.

The secondary conduit is, according to some embodiments, configured to redistribute (e.g., balance) the pressure of the gas delivered to the outlet openings of the primary conduit. Not wishing to be bound by any particular theory, it is believed that when the secondary conduit is at least partially located within the primary conduit, the secondary conduit can act as a pressure redistribution device, which can ensure that the pressure of the gas delivered to the gas outlet openings of the primary conduit is relatively uniform from one opening of the primary conduit to another. By redistributing the pressure in this way, the linear velocity of the gas through the openings of the primary conduit can be relatively uniform. This can lead to the uniform delivery of gas, from the primary conduit to the liquid medium, across multiple openings within the primary conduit. In some cases, by transporting gas uniformly across multiple gas outlet openings, the gas outlet openings can produce gas bubbles that are substantially the same size. By producing gas bubbles at uniform sizes and/or by delivering gas at uniform linear velocities across the primary conduit, one can ensure that the concentration of gas within the vessel containing the gas delivery device (e.g., a reactor such as a bioreactor) is relatively consistent.

The secondary conduit may assume a variety of configurations. In certain embodiments, the secondary conduit is in the form of a tube that is at least partially nested inside the primary conduit. For example, in FIG. 1A, secondary conduit 114 is in the form of a tube located within primary conduit 102. As illustrated in FIGS. 1A-1B, and exterior surface of the wall of secondary conduit 114 is in contact with an interior surface of the wall of primary conduit 102. This can be achieved, for example, by fusing the conduits together, by fabricating the conduits such that they are co-annular, or by any other suitable method known to those of ordinary skill in the art. In other embodiments, the primary and secondary conduits can be in contact at a common inlet. For example, as illustrated in FIGS. 2A-2B, secondary conduit 114 and primary conduit 102 share a common gas inlet opening 110. In some such embodiments, primary conduit 102 secondary conduit 114 may be fused or otherwise integrated with each other at or near gas inlet opening 110. In some such embodiments, aside from the contact near the gas inlet opening, the exterior surface of the wall of the secondary conduit may be free of contact with the interior surface of the wall of the primary conduit.

In the exemplary embodiments of FIGS. 1A-1B and 2A-2B, the primary and secondary conduits are both circular in cross-sectional shape. However, in other embodiments, the cross-sections of the primary and secondary conduits may be of any other shape (e.g., substantially square, substantially rectangular, having five or more sides, or any other shape). In addition, the cross-sectional shape of the primary conduit may be the same as or different from the cross-sectional shape of the secondary conduit.

Figure 3A:
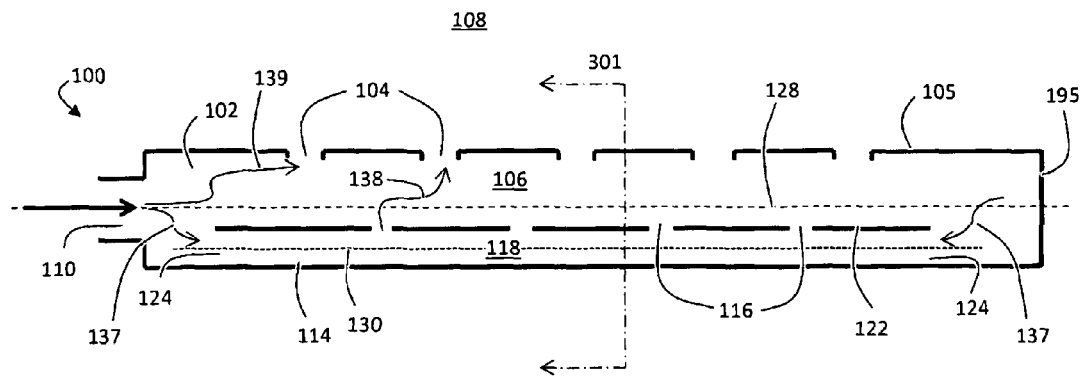
FIGS. 3A-3B are, according to some embodiments, cross-sectional schematic illustrations of a device for producing bubbles of gas within a liquid.
Figure 3B:
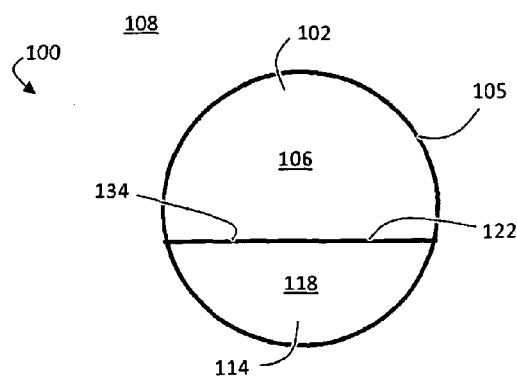

In some embodiments, the secondary conduit may correspond to a portion of the interior of the primary conduit that is separated from the remaining portion of the interior of the primary conduit. In certain embodiments, the secondary conduit is defined by at least one partition separating an interior portion of the secondary conduit from an interior portion of the primary conduit. One example of such an arrangement is illustrated in FIGS. 3A-3B. (As with FIGS. 1A-1B and 2A-2B, the cross-section illustrated in FIG. 3B is perpendicular to the view illustrated in FIG. 3A and along section 301.) In FIG. 3A, secondary conduit 114 is formed by arranging at least one partition 134 such that they define interior flow pathway 118 secondary conduit 114, as distinct from the rest of internal flow pathway 106 of primary conduit 102.

Figure 3C:
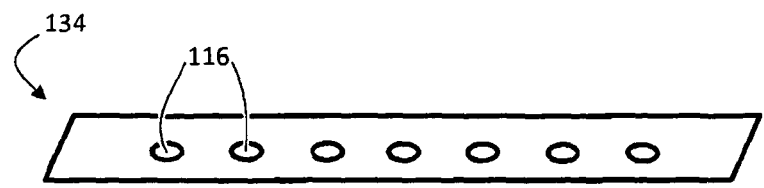
FIGS. 3C-3D are perspective view schematic illustrations of partitions that may be used to define a secondary conduit, according to certain embodiments.
Figure 3D:
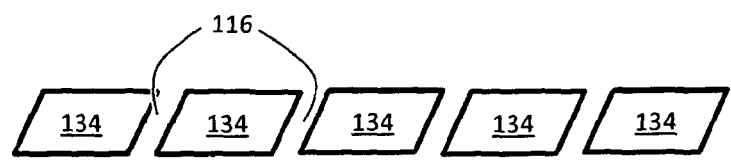

The arrangement illustrated in FIG. 3A-3B can be realized using one or more partitions. Examples of such partitions are shown in FIGS. 3C-3D. FIG. 3C is a perspective view schematic illustration of exemplary partition 134 including a plurality of openings 116 (which can form the openings of the secondary conduit). Partition 134 in FIG. 3C can be inserted into primary conduit 102 such that a single partition defines secondary conduit as well as the plurality of openings in the secondary conduit. As another example, FIG. 3D is a perspective view schematic illustration of a series of partitions 134. In some such embodiments, spacings 116 between the partitions define the openings of the secondary conduit. Combinations of the embodiments illustrated in FIG. 3C and FIG. 3D are also possible. For example, the secondary conduit can be defined by a plurality of partitions that have openings within their surfaces (as illustrated in FIG. 3C) and that are spaced apart from each other (as illustrated in FIG. 3D).

As illustrated in FIGS. 3A-3D, partition(s) 134 are substantially flat. In other embodiments, partition(s) 134 can be curved. A "substantially flat" object is an object having two opposing, substantially planar surfaces that are substantially parallel. Two surfaces may be substantially parallel when an angle between the surfaces is less than 5°, less than 3°, less than 2°, or less than 1°. Curved objects are objects that are not substantially flat.

In FIG. 3B, partition(s) 134 span from one wall portion of primary conduit 102 to a second wall portion of primary conduit 102. In other embodiments, the partition could be arranged such that it contacts the primary conduit at only one location, or in three or more locations.

In some embodiments, a longitudinal axis of the primary conduit is substantially parallel to a longitudinal axis of the secondary conduit. Generally, two lines (e.g., longitudinal axes) are "substantially parallel" to each other when the lines define an angle of less than or equal to about 15°. In certain embodiments, two substantially parallel lines (e.g., longitudinal axes) define an angle of less than or equal to about 10°, less than or equal to about 5°, less than or equal to about 2°, or less than or equal to about 1°. In FIGS. 1A and 3A, for example, longitudinal axis 128 of primary conduit 102 is substantially parallel to longitudinal axis 130 of secondary conduit 114. In FIG. 2A primary conduit 102 and secondary conduit 114 share a common longitudinal axis (denoted by both 128 and 130), and therefore have parallel longitudinal axes.

According to certain embodiments, at least a portion of the longitudinal axis of the secondary conduit is arranged in a side-by-side fashion with the longitudinal axis of the primary conduit. For example, in certain embodiments, at least about 50%, at least about 75%, or at least about 90% of the portion of the length of the secondary conduit that includes its gas outlet openings is arranged such that the longitudinal axis of such portion is in a side-by-side configuration with the longitudinal axis of the length of the primary conduit that includes its gas outlet openings. In FIGS. 1A, 2A, and 3A, for example, 100% of the portion of the length of secondary conduit longitudinal axis 130 that includes secondary conduit gas outlet openings 116 is arranged such that it is in a side-by-side configuration with the length of primary conduit longitudinal axis 128 that includes primary conduit gas outlet openings 104.

As noted above, the gas delivery devices described herein may be used to deliver a gas (e.g., in the form of bubbles, streams, or any other form) to a liquid. In certain embodiments, the gas delivery devices can be used to deliver gas to a liquid medium within a reactor, such as a bioreactor. For example, certain of the gas delivery devices described herein can be used as spargers, delivering bubbles of gas to a liquid medium within a bioreactor or other chemical reactor.

An exemplary description of the operation of a gas delivery device, according to certain embodiments, follows. Certain embodiments comprise transporting gas through a gas inlet opening of the primary conduit. For example, a source of gas (e.g., a compressed gas cylinder or other suitable gas source) may be fluidically connected to the gas inlet opening of the primary conduit. Gas may be transported from the source through the inlet of the primary conduit, for example, by establishing a pressure drop across an opening of the primary conduit. If the source contains pressurized gas, the pressure drop may be established by releasing the gas from the source (e.g., by opening one or more valves associated with the source). In certain embodiments, the gas can be transported by using a pump or any other mechanism may be used to establish a pressure drop of the gas across an inlet of the primary conduit.

Upon entry of the gas into the inlet opening of the primary conduit, at least a portion of the gas may be transported along the internal flow pathway of the primary conduit. In certain embodiments, gas that is transported into the gas inlet opening of the primary conduit is transported from an interior of the primary conduit to an environment outside the primary conduit (e.g., a liquid environment outside the primary conduit) via a plurality of gas outlet openings. For example, in FIGS. 1A, 2A, and 3A, gas may be transported from gas inlet opening 110 of primary conduit 102, through internal flow pathway 106 of primary conduit 102, and subsequently through openings 104 of primary conduit 102 to environment 108 outside primary conduit 102.

According to certain embodiments, at least a portion of the gas that is transported through a gas inlet opening of the primary conduit is transported through a gas inlet opening of the secondary conduit. For example, in FIG. 1A, gas may be transported through inlet 110 of primary conduit 102 and subsequently transported through gas inlet opening 124 of secondary conduit 114, for example, via pathways 137. As another example, in FIG. 3A, gas may be transported through inlet 110 of primary conduit 102 and subsequently transported through gas inlet openings 124 of secondary conduit 114, for example, via pathways 137. In certain embodiments, substantially all of the gas that is transported through the gas inlet opening of the primary conduit is transported through a gas inlet opening of the secondary conduit. For example, as illustrated in FIG. 2A, substantially all of the gas is transported through gas inlet opening 110 of primary conduit 102 is also transported through gas inlet opening 124 of secondary conduit 114, as the primary and secondary conduits share a common gas inlet opening.

In certain embodiments, at least a portion of the gas is transported through the gas outlet openings of the secondary conduit prior to being transported through gas outlet openings of the primary conduit. For example, in FIGS. 1A, 2A, and 3A, gas that is transported through gas inlet openings 124 of secondary conduit 114 can be transported out of openings 116 of secondary conduit 114 prior to being transported through openings 104 of primary conduit 102, for example, via pathway 138.

In some cases, a portion of the gas that is transported through an inlet of the primary conduit may be transported from the inlet of the primary conduit to gas outlet openings of the primary conduit without passing through the secondary conduit. For example, in FIGS. 1A and 3A, a portion of the gas transported through gas inlet opening 110 of primary conduit 102 may be transported through openings 104 of primary conduit 102 without being transported through an internal flow pathway of secondary conduit 114, for example, via pathway 139.

As noted above, in certain embodiments, gas can be transported through the system such that the secondary conduit redistributes (e.g., balances) the pressure of the gas delivered to the gas outlet openings of the primary conduit. In some such embodiments, the hydrostatic pressure of the gas at a relatively high percentage of the gas outlet openings of the primary conduit may be similar. For example, in some embodiments, for at least 80% of the gas outlet openings in the primary conduit (and/or for at least 90%, at least 95%, at least 99%, or for 100% of the gas outlet openings in the primary conduit) the hydrostatic pressure of the gas at the gas outlet opening is within 20% (and/or within 10%, or within 5%) of the average of the hydrostatic pressures of the gas at the gas outlet openings.

According to certain embodiments, the presence of the secondary conduit reduces the difference between the maximum hydrostatic pressure and the minimum hydrostatic pressure observed at the gas outlet openings of the primary conduit, relative to the difference between the maximum and minimum hydrostatic pressures that would be observed in the absence of the secondary conduit but under otherwise identical conditions. The maximum hydrostatic pressure at the gas outlet openings of the primary conduit can be determined by measuring the hydrostatic pressure at each of the gas outlet openings and determining which measured hydrostatic pressure is the largest. The minimum hydrostatic pressure can be determined using the same set of measurements, and determining which measured pressure is the smallest. In some embodiments, the presence of the secondary conduit reduces the difference between the maximum and the minimum hydrostatic pressures at the gas outlets of the primary conduit by at least about 25%, at least about 50%, at least about 75%, at least about 90%, or more, relative to the difference between the maximum and minimum hydrostatic pressures that would be observed in the absence of the secondary conduit but under otherwise identical conditions.

In some embodiments, the pressure redistribution (e.g., balancing) can result in relatively consistent linear gas velocities through the gas outlet openings. For example, in some embodiments, for at least 80% of the gas outlet openings in the primary conduit (and/or for at least 90%, at least 95%, at least 99%, or for 100% of the gas outlet openings in the primary conduit) gas is transported through the gas outlet opening at a linear velocity that is within 20% (and/or within 10%, or within 5%) of the average of the linear velocities at which gas is transported through the gas outlet openings. The linear velocity of gas through a gas outlet opening ($v_{Lin}$) refers to the average magnitude of the velocity of gas as it exits the outlet opening, and is determined as follows:

$$v_{Lin} = \frac{F_{Vol}}{A} \quad [1]$$

wherein $F_{vol}$ is the volumetric flow rate of the gas through the outlet opening at steady state, and A is the outermost cross-sectional area of the opening (i.e., the cross-sectional area formed by the outlet opening on the outer surface of the wall of the primary conduit). The average of the linear velocities at which gas is transported through the gas outlet openings ($v_{Lin,Avg}$) is calculated as a mathematical mean, as follows:

$$v_{Lin,Avg} = (\Sigma_{i=1}^{n} v_{Lin,i})/n \quad [2]$$

wherein $v_{Lin,i}$ is the linear velocity of gas at each outlet (indexed as i), and n is the number of gas outlets. That is to say, the average of the linear velocities is calculated by summing the linear velocities at each of the gas outlet openings and dividing the sum by the number of gas outlet openings.

According to certain embodiments, the presence of the secondary conduit reduces the difference between the maximum linear gas velocity and the minimum linear gas velocity observed at the gas outlet openings of the primary conduit, relative to the difference between the maximum and minimum linear gas velocities that would be observed in the absence of the secondary conduit but under otherwise identical conditions. The maximum linear gas velocity at the gas outlet openings of the primary conduit can be determined by measuring the linear gas velocity at each of the gas outlet openings and determining which measured linear gas velocity is the largest. The minimum linear gas velocity can be determined using the same set of measurements, and determining which measured linear gas velocity is the smallest. In some embodiments, the presence of the secondary conduit reduces the difference between the maximum and the minimum linear gas velocity at the gas outlets of the primary conduit by at least about 25%, at least about 50%, at least about 75%, at least about 90%, or more, relative to the difference between the maximum and minimum linear gas velocity that would be observed in the absence of the secondary conduit but under otherwise identical conditions.

The relatively uniform linear velocities and/or hydrostatic pressures across the gas outlet openings described above may be achieved, according to certain embodiments, over a relatively wide range of average linear velocities at which gas is transported through the gas outlet openings ($v_{Lin,Avg}$) (e.g., for all average linear velocities of from about 0.1 m/s to about 40 m/s, or for all average linear velocities of from about 0.1 m/s to about 80 m/s). As one example, in some embodiments, for at least 80% of the gas outlet openings in the primary conduit (and/or for at least 90%, at least 95%, at least 99%, or for 100% of the gas outlet openings in the primary conduit), gas is transported through the gas outlet opening at a linear velocity that is within 20% (and/or within 10%, or within 5%) of the average of the linear velocities at which gas is transported through the gas outlet openings, for all average linear velocities ($v_{Lin,Avg}$) of from about 0.1 m/s to about 40 m/s. That is to say, in some embodiments, when the gas delivery device is operated at all average linear velocities ($v_{Lin,Avg}$) from about 0.1 m/s to about 40 m/s, the linear gas velocities at a relatively large number of gas outlet openings (e.g., at least 80%, or more, as described above) can be relatively close to the average linear gas velocity (e.g., within 20%, or closer, as described above). In certain embodiments, for at least 80% of the gas outlet openings in the primary conduit (and/or for at least 90%, at least 95%, at least 99%, or for 100% of the gas outlet openings in the primary conduit), gas is transported through the gas outlet opening at a linear velocity that is within 20% (and/or within 10%, or within 5%) of the average of the linear velocities at which gas is transported through the gas outlet openings, for all average linear velocities ($v_{Lin,Avg}$) of from about 0.1 m/s to about 80 m/s.

According to certain embodiments, for at least 80% of the gas outlet openings in the primary conduit (and/or for at least 90%, at least 95%, at least 99%, or for 100% of the gas outlet openings in the primary conduit) the hydrostatic pressure of the gas at the gas outlet opening is within 20% (and/or within 10%, or within 5%) of the average of the hydrostatic pressures of the gas at the gas outlet openings, for all average linear gas velocities ($v_{Lin,Avg}$) of from about 0.1 m/s to about 40 m/s. That is to say, in some embodiments, when the gas delivery device is operated at all average linear gas velocities ($v_{Lin,Avg}$) from about 0.1 m/s to about 40 m/s, the hydrostatic pressure of the gas at a relatively large number of gas outlet openings (e.g., at least 80%, or more, as described above) can be relatively close to the average of the hydrostatic pressures of the gas at the outlet openings (e.g., within 20%, or closer, as described above). In certain embodiments, for at least 80% of the gas outlet openings in the primary conduit (and/or for at least 90%, at least 95%, at least 99%, or for 100% of the gas outlet openings in the primary conduit), the hydrostatic pressure of the gas at the gas outlet opening is within 20% (and/or within 10%, or within 5%) of the average of the hydrostatic pressures of the gas at the gas outlet openings, for all average linear velocities ($v_{Lin,Avg}$) of from about 0.1 m/s to about 80 m/s.

According to certain embodiments, during operation of the gas delivery device, gas is transported through each of the gas outlet openings of the primary conduit. In some such embodiments, there is substantially no weeping in any of the gas outlet openings of the primary conduit.

In some embodiments, the gas delivery systems described herein can be configured to produce gas bubbles within the liquid medium that are substantially monodisperse. For example, in some embodiments, the gas bubbles formed by the gas delivery device can have a distribution of cross-sectional diameters (and/or volumes) such that at least about 50%, at least about 75%, at least about 85%, at least about 90%, at least about 95%, or at least about 99% of the gas bubbles have a cross-sectional diameter that is no more than about 25% different, no more than about 20% different, no more than about 10% different, or no more than about 5% different from the average diameter of the gas bubbles formed by the gas delivery device. As used herein, the cross-sectional diameter of a spherical gas bubble is the diameter that passes through the geometric center of the spherical gas bubble, and the cross-sectional diameter of a non-spherical gas bubble is the diameter of a theoretical spherical gas bubble having the same volume as the non-spherical gas bubble.

The gas delivery devices described herein may be configured to produce gas bubbles having any suitable size. In certain embodiments, a relatively large percentage of the bubbles generated by the gas delivery device are sufficiently large that they do not cause damage and/or death of cells within the liquid medium to which the gas is delivered. For example, in certain embodiments, at least about 50%, at least about 75%, at least about 90%, or at least about 99% of the gas bubbles generated by the gas delivery device have a cross-sectional diameter of at least about 2 mm, at least about 5 mm, or at least about 1 cm. In some embodiments, at least about 50%, at least about 75%, at least about 90%, or at least about 99% of the volume that is occupied by the gas bubbles generated by the gas delivery device is made up of bubbles having a cross-sectional diameter of at least about 2 mm, at least about 5 mm, or at least about 1 cm.

Gas outlet openings 104 can have any suitable cross-sectional shape in the wall in which they are located. For example, the gas outlet openings may form a substantially circular shape, a substantially elliptical shape, a polygonal shape (e.g., substantially square, substantially rectangular, having five or more sides, and the like), or any other shape in the wall of the primary conduit.

Figure 4A:
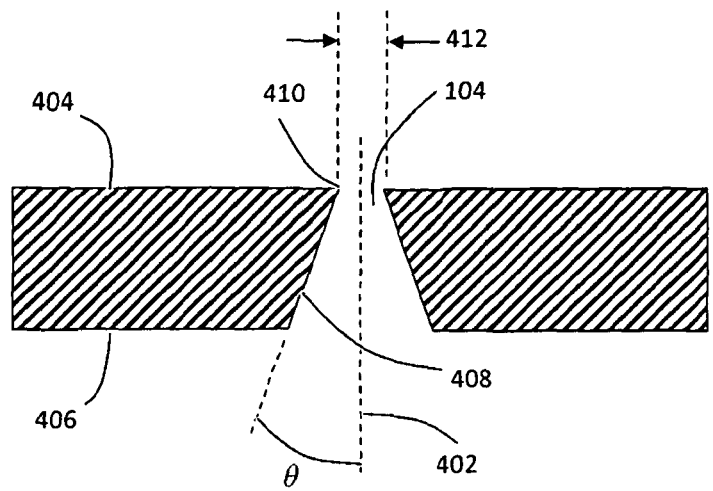
FIGS. 4A-4B are cross-sectional schematic illustrations showing the profiles of exemplary openings within a conduit of a gas delivery device.

The gas outlet openings of the primary conduit and/or the secondary conduit have, in certain embodiments, a cross-sectional shape that tapers in size along the length of a longitudinal axis of the gas outlet openings. The longitudinal axis of a gas outlet opening runs through the geometric center of the gas outlet opening, and is oriented in a direction perpendicular to the external surface of the conduit at the geometric center of the gas outlet opening. For example, referring to FIG. 4A, outlet opening 104 in wall 105 of conduit 102 has longitudinal axis 402. In FIG. 4A, the cross-sectional shape of outlet opening 104 is tapered along longitudinal axis 402 such that the outlet opening is narrower at external surface 404 of conduit 102 than it is at internal surface 406 of conduit 102. As another example, in FIG. 4B, the cross-sectional shape of outlet opening 104 is tapered along longitudinal axis 402 such that the outlet opening is wider at external surface 404 of conduit 102 than it is at internal surface 406 of conduit 102.

In some embodiments, the sidewall of the gas outlet openings in the primary conduit and/or the secondary conduit can form an angle relative to the longitudinal axes of the gas outlet openings. For example, in FIGS. 4A-4B, sidewalls 408 of gas outlet openings 104 form angle θ relative to longitudinal axes 402. In certain embodiments in which the gas outlet openings are angled, the angle formed between the sidewalls of the gas outlet openings and the longitudinal axes of the gas outlet openings can be at least about 1°, at least about 2°, at least about 5°, at least about 10°, at least about 15°, and/or, in some embodiments, up to about 120°, up to about 150°, or more.

The use of tapered gas outlet openings is not required, and in some embodiments, the cross-sectional shape of the gas outlet openings can have sizes and/or shapes that do not taper or do not substantially taper along the length of the longitudinal axis of the gas outlet opening.

The gas outlet openings of the primary and/or secondary conduits can be spaced in any suitable manner. In some embodiments, at least about 50%, at least about 75%, at least about 90%, or at least about 99% of the gas outlet openings of the primary conduit and/or the secondary conduit are substantially evenly spaced. Gas outlet openings (or a subset of gas outlet openings) are substantially evenly spaced when none of the gas outlet openings has a nearest neighbor distance that is more than 20% different from the average of the nearest neighbor distances of the gas outlet openings. In some embodiments, none of the gas outlet openings within the group of substantially evenly spaced gas outlet openings has a nearest neighbor distance that is more than 10%, more than 5%, or more than 1% different from the average of the nearest neighbor distances of the gas outlet openings within the group. In certain embodiments, the average nearest neighbor distance between the gas outlet openings of the primary conduit and/or the secondary conduit is at least about 1 mm, at least about 5 mm, or at least about 10 mm (and/or, in some embodiments, up to about 100 mm, up to about 1000 mm, or more).

In certain embodiments, the gas outlet openings of the primary conduit and/or the secondary conduit can be arranged such that gas is expelled from each of the gas outlet openings in substantially the same direction (e.g., in substantially parallel directions). This may be achieved, for example, by arranging the longitudinal axes of the gas outlet openings of the primary conduit such that they are substantially parallel.

The primary conduit can have any suitable size. In some embodiments, the cross-sectional area of the internal flow pathway of the primary conduit (which includes the cross-sectional area of any secondary conduits nested within the primary conduit) is at least about 1 mm$^2$, at least about 5 mm$^2$, at least about 10 mm$^2$, at least about 1 cm$^2$, or at least about 10 cm$^2$ (and/or, in some embodiments, up to about 100 cm$^2$, up to about 1000 cm$^2$, or more). In certain instances, the size of the primary conduit can be selected based on one or more of the properties of the medium in which it is to be positioned. For example, the size of the primary conduit could be selected based on the volume of liquid media in which it is placed.

The primary conduit can also have any suitable cross-sectional shape. In certain embodiments, the primary conduit has a substantially circular cross-sectional shape. Other suitable cross-sectional shapes include, but are not limited to, a substantially elliptical shape, a polygonal shape (e.g., substantially square, substantially rectangular, having five or more sides, and the like), or any other shape.

The secondary conduit can also have any suitable size. In some embodiments, the cross-sectional area of the internal flow pathway of the secondary conduit is at least about 1 mm$^2$, at least about 5 mm$^2$, at least about 10 mm$^2$, at least about 1 cm$^2$, or at least about 10 cm$^2$ (and/or, in some embodiments, up to about 100 cm$^2$, up to about 1000 cm$^2$, or more). In certain embodiments, the cross-sectional area of the internal flow pathway of the secondary conduit can be selected such that it is neither too large nor too small when compared to the overall cross-sectional area of the primary conduit. In some embodiments, the ratio of the cross-sectional area of the secondary conduit to the cross-sectional area of the primary conduit is at least about 1:50, such as from about 1:20 to about 1:1.2.

The secondary conduit can also have any suitable cross-sectional shape. In certain embodiments, the secondary conduit has a substantially circular cross-sectional shape (e.g., as illustrated in FIGS. 1A-1B). Other suitable cross-sectional shapes include, but are not limited to, a substantially elliptical shape, a polygonal shape (e.g., regular or irregular polygonal, including substantially square, substantially rectangular, having five or more sides, and the like), or any other shape.

In some embodiments, the secondary conduit can have the same cross-sectional shape as the primary conduit. In other embodiments, the secondary conduit and the primary conduit have different cross-sectional shapes.

According to certain embodiments, the gas delivery device can comprise a primary and/or a secondary conduit with substantially linear longitudinal axes (as might be observed, for example, in tubular spargers). Examples of such gas delivery devices are illustrated in FIGS. 1A-1B, 2A-2B, and 3A-3B. In some embodiments, the longitudinal axes of the primary conduit and/or the secondary conduit can be curved (e.g., substantially circular, substantially elliptical, or any other curved shape), bent (e.g., in the shape of a regular or irregular polygon having any number of sides, or in any other shape including one or more angles), or any other suitable shape.

Figure 5:
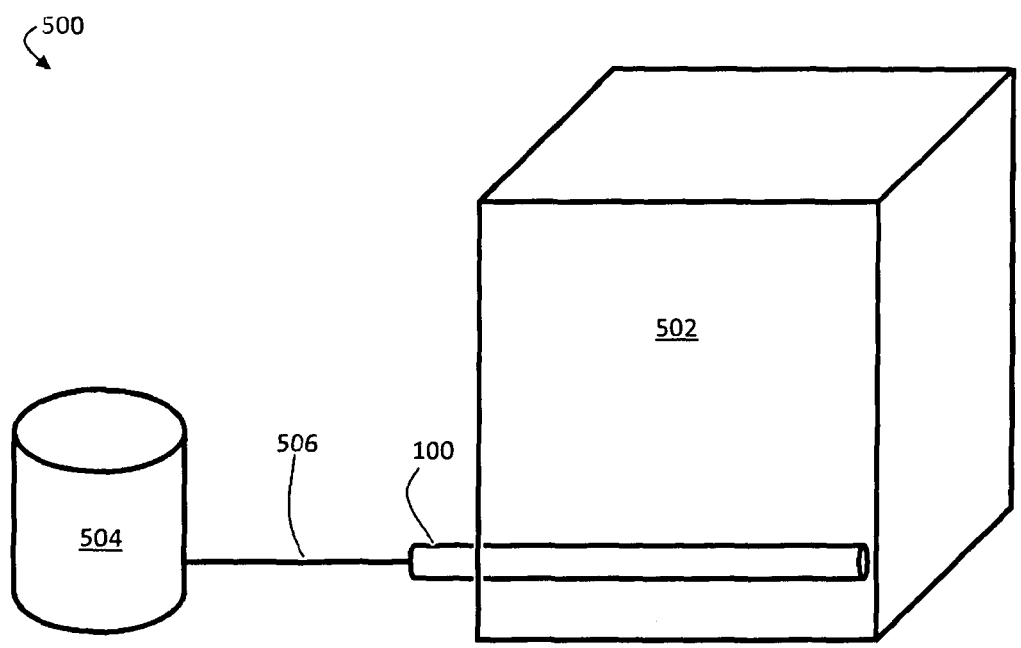
FIG. 5 is a perspective view schematic illustration of a chemical reactor system (e.g., bioreactor) in which a device for producing bubbles of a gas within a liquid is employed, according to certain embodiments.

A variety of systems can, according to certain embodiments, benefit from the use of certain of the gas delivery devices described herein. In some embodiments, the gas delivery system can be part of a chemical reactor. For example, in certain embodiments, the device for producing bubbles of a gas within a liquid is part of a bioreactor. FIG. 5 is a perspective view schematic illustration of a reactor system 500, according to certain embodiments. In FIG. 5, reactor system 500 includes vessel 502 which contains a liquid suitable for performing one or more chemical reactions (e.g., biochemical reactions and/or non-biological chemical reactions). System 500 also comprises device 100 for producing bubbles of gas within the liquid contained within vessel 502. Device 100 can be fluidically connected to source 504 of gas, for example, via conduit 506.

Device 100 in FIG. 5 can correspond to any of the gas delivery devices described elsewhere herein, including any of the gas delivery devices illustrated in FIGS. 1A-1B, 2A-2B, and 3A-3B.

Operation of reactor system 500 may proceed, according to one set of embodiments, as follows. A liquid medium including at least one reactant (e.g., a biological cell or other reactant) can be contained within vessel 502. Vessel 502 may be subject to conditions (e.g., temperature, pressure, fluid recirculation, etc.) suitable for performing a chemical reaction. Gas can be supplied to the liquid medium within vessel 502, from source 504, through gas delivery device 100. For example, a valve may be opened that causes gas from source 504 to be transported through conduit 506, through gas delivery device 100, and to the liquid medium within vessel 502. Other actuation mechanisms could also be used. The gas delivered by gas delivery device 100 may be used, in certain embodiments, as a reactant in the chemical reaction performed within vessel 502. For example, the gas may comprise oxygen and/or carbon dioxide that can be consumed by a cell during a cell culture process.

Reactor system 500 may be configured to perform any suitable chemical reaction. In certain embodiments, the reactor system can be a bioreactor system (e.g., a system configured to perform a reaction involving at least one biological cell). In some embodiments, the bioreactor system is configured to perform a biochemical reaction in which a biological cell and/or at least one biochemically active substance derived from a biological cell is used as a reactant.

In certain embodiments, the bioreactor system is configured to perform cell culture (including the growth of single cells and/or the growth of tissues). The bioreactor system could also be configured to perform, for example, a biochemical reaction in which a cell consumes one or more reaction products. For example, the bioreactor may be part of a sewage treatment process. In some embodiments, the bioreactor may be part of a process for the production of proteins (e.g., therapeutic proteins). In some embodiments, the bioreactor can be a fermentor. The biochemical reaction (e.g., cell growth) performed in the bioreactor may be aerobic or anaerobic. In some embodiments in which aerobic biochemical reactions are performed, the bioreactor system can include a gas delivery device (e.g., any of gas delivery devices 100 described elsewhere here) configured to introduce oxygen to the liquid medium within the bioreactor. In some embodiments in which anaerobic biochemical reactions are performed, the bioreactor system can include a gas delivery device (e.g., any of gas delivery devices 100 described elsewhere here) configured to introduce a non-oxygen gas (e.g., carbon dioxide, nitrogen) to the liquid medium within the bioreactor.

The use of gas delivery systems including a secondary conduit at least partially contained within the primary conduit can be particularly useful, according to certain embodiments, in bioreactor systems in which cells are employed as reactants and/or are produced as products. In some such systems, locating the secondary conduit within the primary conduit can reduce or eliminate the buildup of cells and/or cell products on external surfaces of the gas delivery system, relative to systems in which the secondary conduit is located outside the primary conduit. Preventing buildup of reaction product on the outside of the gas delivery device can reduce the frequency of cleaning, thereby reducing the amount of time that the bioreactor system must be shut down.

Chemical reactor system 500 can be used, according to certain embodiments, to perform biochemical reactions using any types of cells. For example, in some embodiments, a prokaryotic cell and/or a eukaryotic cell can participate in a reaction within the chemical reactor system. In some embodiments, a bacterium (e.g., *E. coli*) or other single-cell organism, a plant cell, and/or an animal cell can participate in a reaction within the chemical reactor system. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. In some embodiments, the cell can be a human cell. In some embodiments, the cell may be a hamster cell, such as a Chinese hamster ovary (CHO) cell, an NS0 cell, and/or a Human Embryonic Kidney 293 (HEK293) cell. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, an osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. Any of these types of cells can be produced, according to certain embodiments, as part of a cell culture system involving chemical reactor system 500.

Vessel 502 can contain any liquid medium suitable for performing a chemical reaction (e.g., a biochemical reaction). In some embodiments, the liquid medium may contain a sugar (e.g., glucose), a nitrogen source (such as ammonia and/or or amino acids), and/or a salt. In some embodiments, the liquid medium comprises one or more essential amino acids and/or cofactors. In some embodiments, the liquid medium comprises a liquid cell growth medium containing at least one nutrient consumed by a biological cell during growth. Those of ordinary skill in the art, given the present disclosure and the chemical reaction pathway that is desired to be performed, would be capable of selecting a suitable liquid medium for use in the chemical reactor system. It should be understood that the gas delivery systems described herein are not limited to use in reactors, and may be used in other non-reactor systems.

According to certain embodiments, the gas delivery system can be used to deliver oxygen to a liquid. In addition to delivering oxygen to reactors (such as bioreactors) oxygen delivery may be useful in aquariums, aerators, and a number of other devices. In some embodiments, the gas delivery system can be used to deliver carbon dioxide to a liquid. In addition to delivering carbon dioxide to reactors, such delivery may be useful, for example, to carbonate beverages.

Certain embodiments are related to inventive configurations (e.g., spacings and/or sizing) of gas outlet openings in one or more conduits of the gas delivery device (e.g., the primary conduit and/or, when present, the secondary conduit). In addition, some embodiments are related to inventive arrangements for joining a gas delivery device is to a vessel, which may be part of, for example, a reactor such as a bioreactor. Certain embodiments are related to the orientation of the gas delivery device and/or its components (e.g., during operation). The inventive gas outlet opening configurations, arrangements for joining the gas delivery device to a vessel, and/or orientations of the gas delivery device described herein can be used in combination with any of the embodiments described above or elsewhere herein. In addition, the presence of a secondary conduit is optional in embodiments in which inventive configurations of gas outlet openings, inventive arrangements for joining the gas delivery device to a vessel, and/or inventive orientations of the gas delivery device are employed. Accordingly, inventive configurations of gas outlet openings, inventive arrangements for joining the gas delivery device to a vessel, and/or inventive orientations of the gas delivery device may be employed in a gas delivery device that employs a single conduit (which may be arranged, for example, as described above with respect to the primary conduit) as well as in a gas delivery device that employs multiple conduits (e.g., a gas delivery device including at least a primary conduit and a secondary conduit, including the examples described above and elsewhere herein).

In certain embodiments, the cross-sectional diameter of the gas outlet openings of a conduit of the gas delivery device can be selected to produce bubbles of a desirable size. This may be useful, for example, when one wishes to reduce (e.g., minimize) the amount of damage imparted to cells within the reactor vessel.

According to certain embodiments, the average of the cross-sectional diameters of the gas outlet openings in the conduit of the gas delivery device (e.g., the primary conduit, which may or may not include a nested secondary conduit) can be less than about 2.5 mm, less than about 2.4 mm, less than about 2.3 mm, less than about 2.2 mm, less than about 2.1 mm, less than about 2.0 mm, less than about 1.9 mm, less than about 1.8 mm, less than about 1.7 mm, less than about 1.6 mm, less than about 1.5 mm, less than about 1.4 mm, less than about 1.3 mm, less than or equal to about 1.2 mm, less than about 1.1 mm, less than about 1.0 mm, less than about 0.9 mm, less than about 0.8 mm, less than about 0.7 mm, less than about 0.6 mm, less than about 0.5 mm, or less (and/or, in some embodiments, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, at least about 1.5 mm, or greater). It should be understood that the ranges recited above can be employed alone or in any combination of a lower bound range and an upper bound range. For example, in one set of embodiments, the average of the cross-sectional diameters of the gas outlet openings in the conduit of the gas delivery device is less than about 2.5 mm. In some embodiments, the average of the cross-sectional diameters of the gas outlet openings in the conduit of the gas delivery device is less than about 2.0 mm. In one set of embodiments, the average of the cross-sectional diameters of the gas outlet openings in the conduit of the gas delivery device is less than about 1.5 mm. As another example, in some embodiments, the average of the cross-sectional diameters of the gas outlet openings in the conduit of the gas delivery device at least about 0.1 mm and less than about 2.5 mm. In some embodiments, the average of the cross-sectional diameters of the gas outlet openings in the conduit of the gas delivery device at least about 0.1 mm and less than about 2.0 mm. In some embodiments, the average of the cross-sectional diameters of the gas outlet openings in the conduit of the gas delivery device at least about 0.1 mm and less than about 1.5 mm. Other combinations of ranges are also possible. In certain embodiments, the average of the cross-sectional diameters of the gas outlet openings in the conduit of the gas delivery device is 1.6 mm. In some embodiments, the average of the cross-sectional diameters of the gas outlet openings in the conduit of the gas delivery device is not 1.6 mm.

Figure 4B:
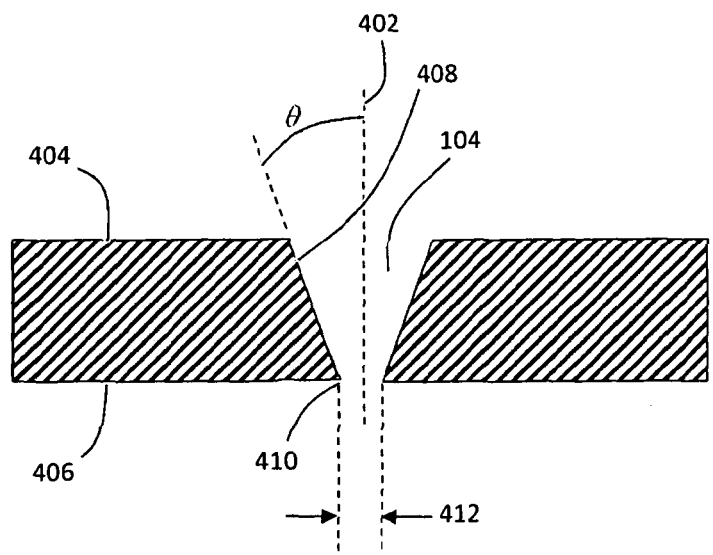

The cross-sectional diameter of a gas outlet opening corresponds to the smallest cross-sectional dimension of the gas outlet opening which extends through the geometric center of the cross-sectional shape of the gas outlet opening and extends perpendicular to the longitudinal axis of the gas outlet opening. For example, in the case of a cylindrical gas outlet opening (e.g., as shown in FIG. 1A), the cross-sectional diameter of the gas outlet opening corresponds to the diameter of the cylinder (shown as dimension 190 in FIG. 1A). As another example, in the case of a tapered gas outlet opening with a circular cross-sectional shape (e.g., as shown in FIGS. 4A-4B), the cross-sectional diameter of the gas outlet opening corresponds to the smallest diameter of the circular cross-sectional shape (which, in the case of FIGS. 4A and 4B, would correspond to the cross-sectional diameter of the gas outlet opening at positions 410, which is indicated as dimensions 412 in FIGS. 4A and 4B). When gas outlet openings with non-circular cross-sections are employed, the cross-sectional diameter of the gas outlet opening (at each position along the longitudinal axis of the gas outlet opening) would correspond to the diameter of a theoretical circle having the same cross-sectional area as the non-circular shape of the opening. As one specific example, when gas outlet openings with elliptical cross-sections are employed, the cross-sectional diameter of the gas outlet opening would correspond to the diameter of a theoretical circle having the same cross-sectional area as the ellipse. It has been found experimentally that by employing relatively small gas outlet openings (including gas outlet openings having cross-sectional diameters within the ranges specified above), bubble formation patterns are generally well-controlled and unified which results in a reduced number of very small bubbles (e.g., having diameters of less than 0.1 mm) generated by the gas delivery device, and, in some cases, the generation of a large number of relatively large bubbles (e.g., bubbles having diameters of 1 to 5 mm). The generation of relatively large bubbles and the reduction in the generation of relatively small bubbles can reduce the amount of biological cell damage while increasing the gas/liquid surface are for mass transfer and meeting increased cell respiratory demand during biochemical reaction processes.

The average of the cross-sectional diameters of a plurality of gas outlet openings is calculated as a number average.

In some embodiments, the gas outlet openings within a conduit of the gas delivery device can have relatively consistently-sized cross-sectional diameters. For example, in some embodiments, at least about 80%, at least about 90%, at least about 95%, at least about 98%, at least about 99%, or substantially all of the gas outlet openings of a conduit of the gas delivery device have cross-sectional diameters that are within about 200%, within about 100%, within about 50%, within about 20%, within about 15%, within about 10%, within about 5%, or within about 1% of the average of the cross-sectional diameters of the gas outlet openings. In certain embodiments, the conduit of the gas delivery device does not include any gas outlet openings having a cross-sectional diameter that is more than about 5 times, more than about 4 times, more than about 3 times, more than about 2 times, more than about 1.5 times, more than about 1.2 times, or more than about 1.1 times the average of the cross-sectional diameters of all gas outlet openings in the conduit. The absence of gas outlet openings with relatively large sizes can prevent excess loss of injected gas via a single gas outlet opening during operation of the gas delivery device. In some embodiments, the end of the conduit opposite the end of the conduit comprising the inlet gas opening does not include a gas outlet opening. For example, in FIGS. 1A and 3A, end 195 of primary conduit 102 does not include a gas outlet opening.

In certain embodiments, the average of the nearest neighbor distances between the gas outlet openings of a conduit of the gas delivery device can be selected to avoid coalescence of bubbles. This may be useful, for example, when one wishes to reduce (e.g., minimize) the amount of damage imparted to cells within the reactor vessel, which has been experimentally found to increase with increased coalescence of bubbles produced by the gas delivery device.

According to certain embodiments, the average of the nearest neighbor distances between the gas outlet openings of a conduit of the gas delivery device (e.g., the primary conduit, which may or may not include a nested secondary conduit) can be at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less). It should be understood that the ranges recited above can be employed alone or in any combination of a lower bound range and an upper bound range. For example, in one set of embodiments, the average of the nearest neighbor distances between the gas outlet openings of a conduit of the gas delivery device is less than about 30 mm. In certain embodiments, the average of the nearest neighbor distances between the gas outlet openings of a conduit of the gas delivery device is at least about 2 mm. In one set of embodiments, the average of the nearest neighbor distances between the gas outlet openings of a conduit of the gas delivery device is at least about 6 mm. In some embodiments, the average of the nearest neighbor distances between the gas outlet openings of a conduit of the gas delivery device is at least about 12 mm. As another example, in some embodiments, the average of the nearest neighbor distances between the gas outlet openings of a conduit of the gas delivery device is at least about 2 mm and less than about 30 mm. In some embodiments, the average of the nearest neighbor distances between the gas outlet openings of a conduit of the gas delivery device is at least about 6 mm and less than about 30 mm. In some embodiments, the average of the cross sectional diameters of the gas outlet openings in the conduit of the gas delivery device at least about 12 mm and less than about 30 mm. Other combinations of ranges are also possible. In certain embodiments, the average of the nearest neighbor distances between the gas outlet openings of a conduit of the gas delivery device is 10 mm. In some embodiments, the average of the nearest neighbor distances between the gas outlet openings of a conduit of the gas delivery device is 5 mm. In certain embodiments, the average of the nearest neighbor distances between the gas outlet openings of a conduit of the gas delivery device is not 10 mm. In certain embodiments, the average of the nearest neighbor distances between the gas outlet openings of a conduit of the gas delivery device is not 5 mm.

The nearest neighbor distance of a particular gas outlet opening corresponds to the smallest distance between the center of that particular gas outlet opening and the center of the gas outlet opening closest to that particular gas outlet opening. For example, in FIG. 1A, gas outlet opening 192 has a nearest neighbor distance indicated by dimension 191, which corresponds to the distance between the center of gas outlet opening 192 and the center of gas outlet opening 193. It has been found experimentally that by employing gas outlet openings that are spaced reasonably far apart (including nearest neighbor distances within the ranges specified above), the degree of coalescence of the bubbles generated by the gas delivery device can be reduced, which can reduce the amount of biological cell damage observed during biochemical reaction processes.

The average of the nearest neighbor distances between the gas outlet openings of a conduit of the gas delivery device is calculated as a number average.

In some embodiments, the gas outlet openings within a conduit of the gas delivery device can be spaced relatively consistently. For example, in some embodiments, at least about 80%, at least about 90%, at least about 95%, at least about 98%, at least about 99%, or substantially all of the gas outlet openings of a conduit of the gas delivery device have nearest neighbor distances that are within about 200%, within about 100%, within about 50%, within about 20%, within about 15%, within about 10%, within about 5%, or within about 1%, of the average of the nearest neighbor distances between the gas outlet openings.

The nearest neighbor distances described above can be used alone or in combination with the ranges of averages of the cross-sectional diameters of the gas outlet openings recited above and elsewhere herein. In some embodiments, the average of the cross-sectional diameters of the gas outlet openings in the conduit of the gas delivery device is at least about 0.8 mm (e.g., at least about 0.8 mm and less than about 2.5 mm, or within any of the average cross-sectional diameter ranges recited elsewhere herein), and the average of the nearest neighbor distances between the gas outlet openings of a conduit of the gas delivery device is at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less). In certain embodiments, the average of the cross-sectional diameters of the gas outlet openings in the conduit of the gas delivery device is less than about 0.8 mm (e.g., at least about 0.1 mm and less than about 0.8 mm, or within any of the average cross-sectional diameter ranges recited elsewhere herein), and the average of the nearest neighbor distances between the gas outlet openings of a conduit of the gas delivery device is at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less).

Figure 6A:
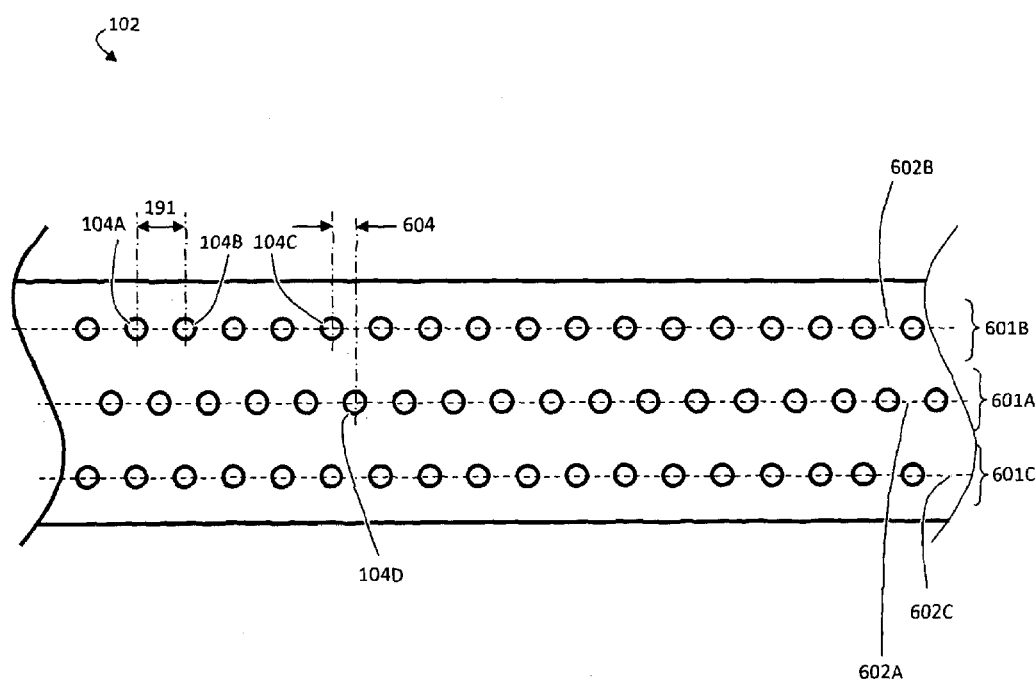
FIG. 6A is a top view schematic illustration of a device for producing bubbles of gas within a liquid, according to certain embodiments.

The gas outlet openings of a conduit of a gas delivery device can be arranged in one or more rows, in some embodiments. For example, in certain embodiments, the gas outlet openings in the primary conduit (which may or may not have a nested secondary conduit) are arranged in at least one row extending along the longitudinal axis of the primary conduit. One example of such an arrangement is illustrated in FIG. 6A, which is a top view of an exemplary conduit of a gas delivery device. The conduit illustrated in FIG. 6A can correspond to, for example, any of the primary conduits illustrated in FIGS. 1A, 2A, and/or 3A (which can include nested secondary conduits). The conduit illustrated in FIG. 6A could also be a single conduit in which a secondary conduit is not nested.

In some embodiments, the primary conduit includes a single row of gas outlet openings. The primary conduit can also comprise, in certain embodiments, two or more rows of gas outlet openings. For example, in some embodiments, the primary conduit comprises a first row of gas outlet openings extending along the longitudinal axis of the primary conduit, and a second row of gas outlet openings extending along the longitudinal axis of the primary conduit. In FIG. 6A, for example, primary conduit 102 comprises first row 601A of gas outlet openings 104. Primary conduit 102 can also comprise optional second row 601B of gas outlet openings 104 and/or optional third row 601C of gas outlet openings 104. In FIG. 6A, each of rows 601A, 601B, and 601C are arranged a direction that extends along the longitudinal axis of the primary conduit. For example, row 601A comprises gas outlet openings arranged along a direction indicated by dotted line 602A, which extends along the longitudinal axis of primary conduit 102. (To maintain clarity in the figures, the longitudinal axis of primary conduit 102 in FIG. 6A is not illustrated separately, as the longitudinal axis of primary conduit 102 overlaps with dotted line 602A in FIG. 6A). In addition, in FIG. 6A, row 601B comprises gas outlet openings arranged along a direction indicated by dotted line 602B, which extends along the longitudinal axis of primary conduit 102, and row 601C comprises gas outlet openings arranged along a direction indicated by dotted line 602C, which extends along the longitudinal axis of primary conduit 102. While primary conduits comprising one row, two rows, and three rows have been described, the primary conduit can also include more rows. In some embodiments, the primary conduit comprises at least one row, at least two rows, at least three rows, at least four rows, at least five rows, or at least 10 rows of gas outlet openings, for example, having any of the layouts or gas outlet opening properties described elsewhere herein.

In some embodiments, the direction along which the row(s) of gas outlet openings extends is substantially parallel to or concentric with the portion of the longitudinal axis of the primary conduit along which the row extends. For example, in certain cases in which the primary conduit has a linear or substantially linear longitudinal axis, the direction along which the row(s) of gas outlet openings extend can also be linear or substantially linear, and the row can extend in a direction that is substantially parallel to the longitudinal axis of the primary conduit. For example, in FIG. 6A, each of rows 601A, 601B, and 601C comprise gas outlet openings that extend in a direction (602A, 602B, and 602C, respectively) that is substantially parallel to the longitudinal axis of primary conduit 102. In certain embodiments in which the primary conduit has a curved longitudinal axis, the direction along which the row(s) of gas outlet openings extend can also be curved, and the row can extend in a direction that is substantially concentric with the curvature of the longitudinal axis of the primary conduit. In certain embodiments, and as discussed in more detail below, the positions of the gas outlet openings in one row can be offset, in a direction along the longitudinal axis of the primary conduit, relative to the positions of the gas outlet openings of another (e.g., adjacent) row.

Each row of gas outlet openings in the primary conduit can include any suitable number of gas outlet openings. In certain embodiments, at least one row of gas outlet openings includes at least about 10 gas outlet openings, at least about 20 gas outlet openings, at least about 40 gas outlet openings, or at least about 75 gas outlet openings (and/or, in certain embodiments, up to about 85 gas outlet openings, up to about 100 gas outlet openings, up to about 150 gas outlet openings, up to about 200 gas outlet openings, up to about 500 gas outlet openings, or more).

In some embodiments, the primary conduit comprises three rows of gas outlet openings (e.g., each row having at least about 10 gas outlet openings, at least about 20 gas outlet openings, at least about 40 gas outlet openings, or at least about 75 gas outlet openings, and/or, in certain embodiments, up to about 85 gas outlet openings, up to about 100 gas outlet openings, up to about 150 gas outlet openings, up to about 200 gas outlet openings, up to about 500 gas outlet openings, or more) and a fourth row of gas outlet openings (e.g., at least about 2, at least about 3, at least about 4, at least about 5, and/or, up to about 7, up to about 8, up to about 9, and/or up to about 10 gas outlet openings, or more). In some embodiments, the fourth row of gas outlet openings (which includes fewer gas outlet openings than the other three rows) can be configured to drain liquid from the gas delivery device during cleaning. Additional rows of gas outlet openings are also possible, as explained below.

In some embodiments, within a row(s) (or within all rows) of gas outlet openings in a conduit of the gas delivery device, the average of the cross-sectional diameters of the gas outlet openings can be less than about 2.5 mm, less than about 2.4 mm, less than about 2.3 mm, less than about 2.2 mm, less than about 2.1 mm, less than about 2.0 mm, less than about 1.9 mm, less than about 1.8 mm, less than about 1.7 mm, less than about 1.6 mm, less than about 1.5 mm, less than about 1.4 mm, less than about 1.3 mm, less than or equal to about 1.2 mm, less than about 1.1 mm, less than about 1.0 mm, less than about 0.9 mm, less than about 0.8 mm, less than about 0.7 mm, less than about 0.6 mm, less than about 0.5 mm, or less (and/or, in some embodiments, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, at least about 1.5 mm, or greater).

In some embodiments, within a row(s) (or within all rows) of gas outlet openings within a conduit of the gas delivery device, the gas outlet openings can have relatively consistently-sized cross-sectional diameters. For example, in some embodiments, at least about 80%, at least about 90%, at least about 95%, at least about 98%, at least about 99%, or substantially all of the gas outlet openings within a row(s) (or within each row) of gas outlet openings have cross-sectional diameters that are within about 200%, within about 100%, within about 50%, within about 20%, within about 15%, within about 10%, within about 5%, or within about 1% of the average of the cross-sectional diameters of the gas outlet openings within that row.

In some embodiments, the average of the nearest neighbor distances between the gas outlet openings within a row(s) (or within all rows) of gas outlet openings of a conduit can be at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less).

In some embodiments, within a row(s) (or within all rows) of gas outlet openings of a conduit, the average of the cross-sectional diameters of the gas outlet openings in the row is at least about 0.8 mm (e.g., at least about 0.8 mm and less than about 2.5 mm, or within any of the average cross-sectional diameter ranges recited elsewhere herein), and the average of the nearest neighbor distances between the gas outlet openings of the row is at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less). In certain embodiments, within a row(s) (or within all rows) of gas outlet openings of a conduit, the average of the cross-sectional diameters of the gas outlet openings in the row is less than about 0.8 mm (e.g., at least about 0.1 mm and less than about 0.8 mm, or within any of the average cross-sectional diameter ranges recited elsewhere herein), and the average of the nearest neighbor distances between the gas outlet openings of the row is at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, or more (and/or, according to certain embodiments, less than about 30 mm, less than about 28 mm, less than about 26 mm, less than about 24 mm, less than about 22 mm, less than about 20 mm, or less).

In some embodiments, the gas outlet openings within the row(s) can be substantially evenly spaced. For example, in some embodiments, in some embodiments, at least about 80%, at least about 90%, at least about 95%, at least about 98%, at least about 99%, or substantially all of the gas outlet openings within a row(s) (or within all rows) of gas outlet openings of a primary conduit have nearest neighbor distances that are within about 200%, within about 100%, within about 50%, within about 20%, within about 15%, within about 10%, within about 5%, or within about 1%, of the average of the nearest neighbor distances between the gas outlet openings within the corresponding row. For example, in FIG. 6A, all of the gas outlet openings within row 601A have nearest neighbor distances that are within 1% of the average of the nearest neighbor distances between the gas outlet openings within row 601A. Similarly, in FIG. 6A, all of the gas outlet openings within row 601B have nearest neighbor distances that are within 1% of the average of the nearest neighbor distances between the gas outlet openings within row 601B, and all of the gas outlet openings within row 601C have nearest neighbor distances that are within 1% of the average of the nearest neighbor distances between the gas outlet openings within row 601C. In FIG. 6A, the nearest neighbor distance for gas outlet opening 104A within row 601B is illustrated as dimension 191 (i.e., the distance between the center of opening 104A and the center of its nearest neighbor within row 601B, opening 104B).

In some embodiments, the positions of the gas outlet openings in a second row can be offset, in a direction along the longitudinal axis of the primary conduit, relative to the positions of the gas outlet openings of a first (e.g., adjacent) row. For example, in FIG. 6A, gas outlet openings within second row 601B are offset, in a direction along the longitudinal axis of primary conduit 102, relative to the positions of the gas outlet openings in first row 601A by a distance indicated by dimension 604 in FIG. 6A. Dimension 604 in FIG. 6A corresponds to the center-to-center spacing between gas outlet opening 104C and gas outlet opening 104D, along the longitudinal axis of conduit 102. Experiments have demonstrated that, when the positions of the gas outlet openings in a second row are offset relative to the positions of the gas outlet openings in a first row, the gas bubbles produced from the gas outlet openings in the second row are less likely to coalesce with the gas bubbles produced from the gas outlet openings in the first row. The absence of coalescence can lead to decreased cell death when the gas delivery device is used to deliver gas to cells in a bioreactor, for example.

In some embodiments, the offset distance along the longitudinal axis from the first row of gas outlet openings to the second (e.g., adjacent) row of gas outlet openings can be at least about 0.1 mm, at least about 0.25 mm, at least about 0.5 mm, at least about 1 mm, at least about 1.5 mm, at least about 2 mm, at least about 3 mm, at least about 4 mm, at least about 5 mm, at least about 6 mm, at least about 7 mm, or at least about 8 mm (and/or, in some embodiments, up to about 9 mm, up to about 10 mm, up to about 12 mm, up to about 15 mm, or more). These ranges can be employed alone or in any combination of a lower bound range and an upper bound range.

In some embodiments, the offset distance along the longitudinal axis from the first row of gas outlet openings to the second (e.g., adjacent) row of gas outlet openings can be at least about 0.1 times, at least about 0.25 times, at least about 0.5 times, at least about 0.75 times, or at least about 1 time, at least about 2 times, at least about 3 times, or at least about 4 times the average cross-sectional diameter of the gas outlet openings in the first and second rows (and/or, in some embodiments, the offset distance along the longitudinal axis from the first row of gas outlet openings to the second row of gas outlet openings can be less than or equal to about 12 times, less than or equal to about 10 times, less than or equal to about 9 times, less than or equal to about 8 times, or less than or equal to about 6 times the average cross-sectional diameter of the gas outlet openings in the first and second rows). These ranges can be employed alone or in any combination of a lower bound range and an upper bound range.

As noted above, some embodiments are related to inventive arrangements for joining a gas delivery device is to a vessel. The vessel may be part of, for example, a reactor such as a bioreactor. One example of such a vessel is vessel 502 illustrated in FIG. 5.

In some embodiments, the gas delivery device comprises a vessel connection portion configured to be connected to a vessel. For example, referring to FIG. 6B, gas delivery device 100 comprises a vessel connection portion 610. In some embodiments, the vessel connection portion is elongated (e.g., in the form of an elongated shaft), for example having an aspect ratio (e.g., the ratio of the elongated dimension relative to a dimension perpendicular to the elongated dimension) of at least about 2:1, at least about 5:1 at least about 10:1, at least about 25:1, at least about 100:1, or more. The vessel connection portion can include a longitudinal axis, such as longitudinal axis 612 in FIG. 6B. The vessel connection portion can, according to certain embodiments, be configured to be connected to a source of gas for the gas delivery device. For example, in some embodiments, the vessel connection portion can be connected to source 504 illustrated in FIG. 5. The vessel connection portion can include, in some embodiments, a gas inlet opening of the gas delivery device.

In some embodiments, the vessel connection portion of the gas delivery device comprises a connector, configured to connect the gas delivery device to a vessel (e.g. a wall of a vessel). The connector of the vessel connection portion can comprise a protrusion or indentation, in some embodiments. For example, in FIG. 6B, vessel connection portion 610 comprises flange 614. Flange 614 can be configured to interface with a sidewall that vessel, according to certain embodiments.

Figure 6B:
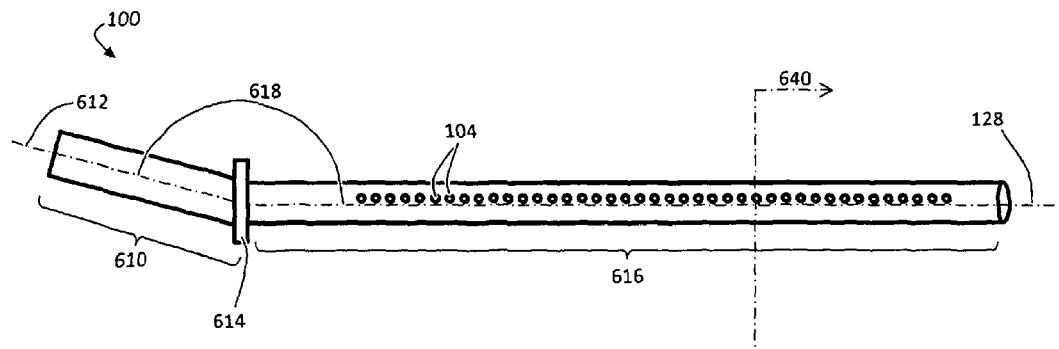
FIG. 6B is, according to some embodiments, a side view schematic illustration of a device for producing bubbles of gas within a liquid.

The gas delivery device can also comprise, in some embodiments, a gas delivery portion. For example, in FIG. 6B, gas delivery device 100 comprises gas delivery portion 616. The gas delivery portion can comprise a plurality of gas outlet openings, which can be used to deliver gas to an environment surrounding the gas delivery device. In some embodiments, the gas delivery portion comprises a conduit, such as any of the primary conduits described herein (optionally, with a secondary conduit nested at least partially within the primary conduit). In FIG. 6B, for example, gas delivery portion 616 comprises a conduit including gas outlet openings 104. The gas delivery portion can be elongated, for example having aspect ratio (e.g., the ratio of the elongated dimension relative to a dimension perpendicular to the elongated dimension) of at least about 2:1, at least about 5:1 at least about 10:1, at least about 25:1, at least about 100:1, or more. The gas delivery portion can also comprise a longitudinal axis. For example, gas delivery portion 616 in FIG. 6B comprises longitudinal axis 128.

Any of the sizes and/or spatial arrangements of gas outlet openings described elsewhere herein can be used in the gas delivery portion of the gas delivery device.

In some embodiments, the longitudinal axis of gas delivery portion is angled relative to the longitudinal axis of the vessel connection portion. For example, in FIG. 6B, longitudinal axis 612 of vessel connection portion 610 is angled relative to longitudinal axis 128 of gas delivery portion 616. In some embodiments, the angle defined between the longitudinal axis of the vessel connection portion and the longitudinal axis of the gas delivery portion can be between about 155° and about 175°, between about 160° and about 170°, between about 161° and about 169°, between about 162° and about 168°, between about 163° and about 167°, or between 164° and about 166°. In some embodiments, the angle defined between the longitudinal axis of the vessel connection portion and the longitudinal axis of the gas delivery portion can be about 165°, as illustrated by angle 618 in FIG. 6B.

In some embodiments, the longitudinal axis of gas delivery portion is angled relative to a line or a plane defined by a row of gas outlet openings on the gas delivery device. In some embodiments, the angle defined between the longitudinal axis of the vessel connection portion and the line or plane defined by a row of gas outlet openings on the gas delivery device is between about 155° and about 175°, between about 160° and about 170°, between about 161° and about 169°, between about 162° and about 168°, between about 163° and about 167°, or between about 164° and about 166°.

Figure 6C:
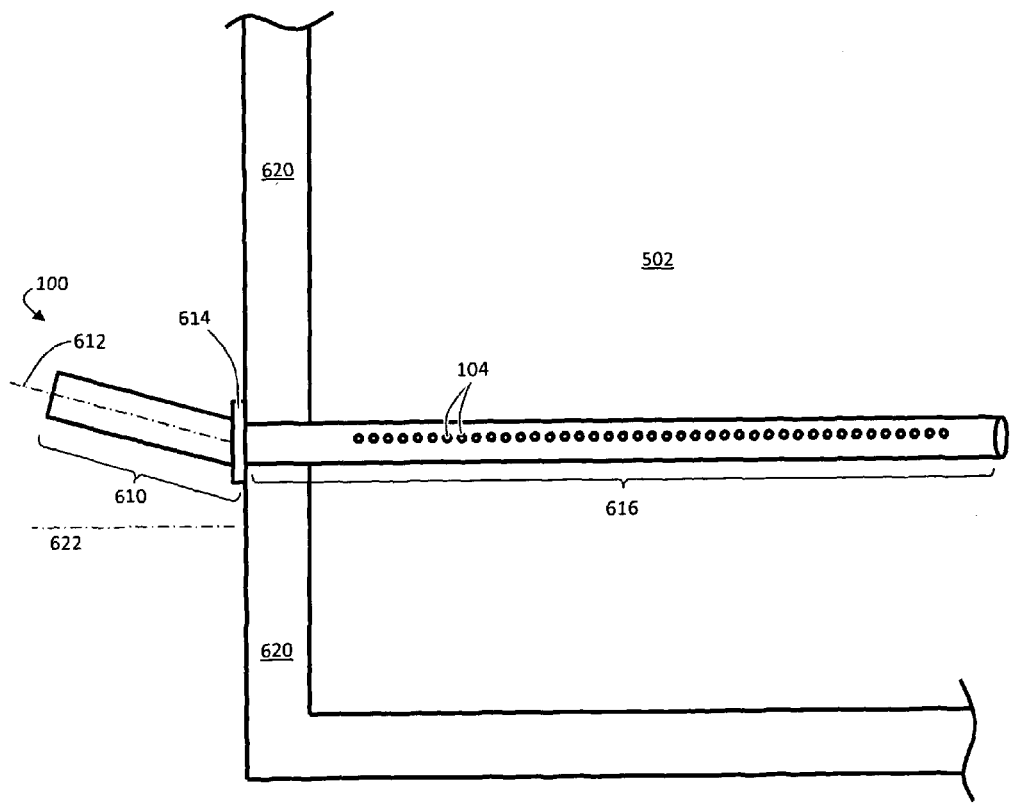
FIG. 6C is a side view schematic illustration, according to one set of embodiments, of a device for producing bubbles of gas within a liquid, connected to a vessel.

As noted above, in some embodiments, the gas delivery device can be configured to be attached to the sidewall of a vessel, such as a reactor. FIG. 6C is a schematic illustration of one such embodiment. In FIG. 6C, gas delivery device 100 is attached to vessel 502 via vessel wall 620. As illustrated in FIG. 6C, gas delivery portion 616 of gas delivery device 100 can extend through the vessel wall 620 and out of vessel 502, and vessel connection portion 610 can be located outside of the vessel. Flange 614 can be used to connect the gas delivery device to the exterior of vessel wall 620.

In some such embodiments, the vessel connection portion can be configured at an angle relative to the sidewall of the vessel. For example, in some embodiments, the longitudinal axis of the vessel connection portion can form an angle of between about 5° and about 25°, between about 10° and about 20°, between about 11° and about 19°, between about 12° and about 18°, between about 13° and about 17°, or between about 14° and about 16° relative to a line extending perpendicularly from the vessel sidewall. For example, in FIG. 6C, longitudinal axis 612 of vessel connection portion 610 forms an angle of about 15° relative to line 622 extending perpendicularly from vessel sidewall 620.

In some embodiments, the gas outlet openings of the gas delivery portion extend in a direction that is substantially horizontal when the gas delivery device is coupled to the vessel. For example, in FIG. 6C, gas outlet openings 104 of gas delivery device 100 extend substantially horizontally within vessel 502. Experiments have demonstrated that configuring the gas delivery device in this way can reduce or eliminate uneven flow through the gas outlet openings of the gas delivery device (as described in more detail below)

while allowing one to connect the gas delivery device to standard openings in vessels such as bioreactor vessels. Without wishing to be bound by any particular theory, it is believed that by angling the gas delivery device in this way, substantially even distribution of gas flow through all gas outlet openings can be achieved. Evenly distributing the flow through all gas outlet openings can help reduce the overall gas entrance velocity.

Certain embodiments are related to the orientation of the gas delivery device and/or its components (e.g., during operation).

In some embodiments, during operation, the gas outlet openings of the primary conduit are arranged such that, from opening to opening, they extend in a direction that is substantially horizontal. This can be achieved, for example, by arranging the longitudinal axis of the primary conduit such that it is substantially horizontal during operation. Gas outlet openings of a conduit are said to extend in a direction that is substantially horizontal when the direction, from opening to opening, in which the gas outlet openings extend is within 5° of horizontal as determined using a level instrument. In some embodiments, the substantially horizontal gas outlet openings can extend within 3°, within 2°, or within 1° of horizontal. It has been discovered that, when the conduit is arranged such that its gas outlet openings extend substantially horizontally, substantially even gas flow rates are observed from each gas outlet opening, even at relatively low linear gas velocities. On the other hand, if the gas outlet openings are arranged along a non-horizontal direction, gas holdup can occur, and some of the holes do not emit gas until relatively high flow rates are employed.

Figure 6D:
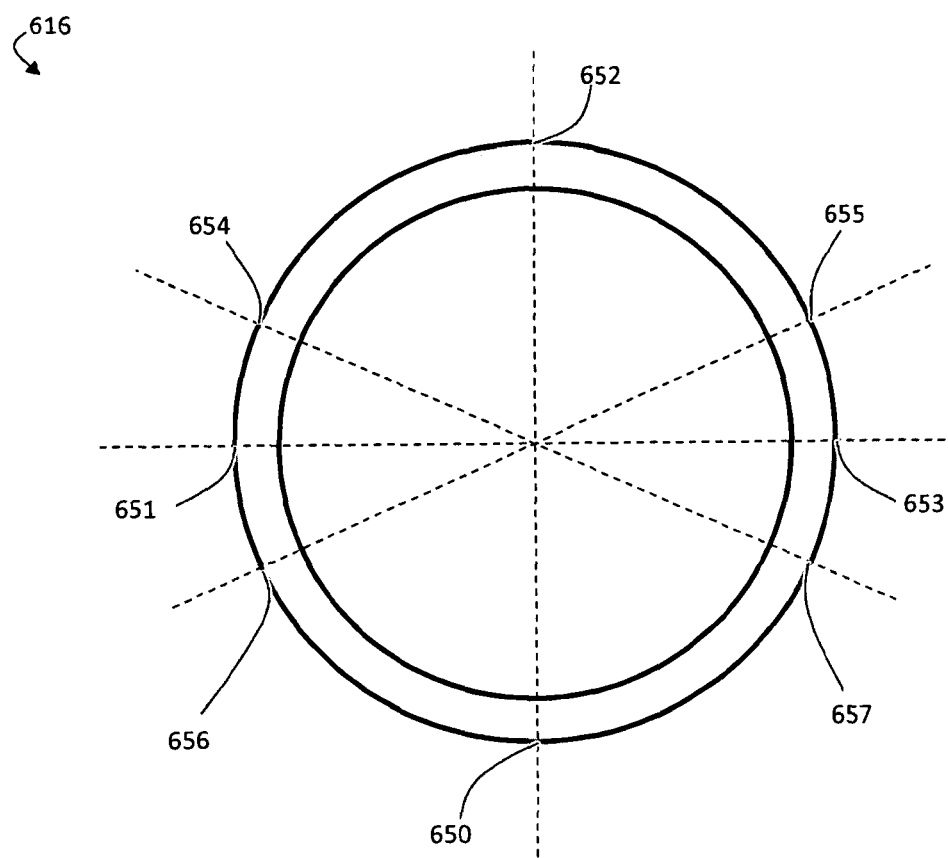
FIG. 6D is, according to certain embodiments, a cross-sectional schematic illustration of a device for producing bubbles of gas within a liquid.

In certain embodiments, rows of gas outlet openings can be spatially distributed around the circumference of a conduit of the gas delivery device in such a way as to avoid agglomeration of bubbles. FIG. 6D is an exemplary cross-sectional schematic illustration of gas delivery portion 616 of gas delivery device 100, taken through section 640 as illustrated in FIG. 6B. In FIG. 6D, position 650 indicates a 0° reference angle (which can correspond to a point facing downward during use of the gas delivery device), position 651 indicates a 90° reference angle, position 652 indicates a 180° reference angle (which can correspond to a point facing upward during use of the gas delivery device), and position 653 indicates a 270° reference angle. In some embodiments, the gas delivery portion includes a first row of gas outlet openings extending in a direction along a longitudinal axis of the primary conduit and a second row of gas outlet openings extending in a direction along a longitudinal axis of the primary conduit, wherein the first and second rows are spaced at least about 30°, at least 40°, at least 50°, or at least 55° apart from each other around the circumference of the gas delivery device, when viewed in cross-section (and/or, in some embodiments, less than about 90°, less than about 80°, less than about 70°, or less than about 65° apart from each other around the circumference of the gas delivery device, when viewed in cross-section). In some such embodiments, a third row of gas outlet openings extending in a direction along the longitudinal axis of the primary conduit can be present. The third row gas outlet openings can be on the opposite side of the first row of gas outlet openings as the second row of gas outlet openings. In some such embodiments, the third row of gas outlet openings is spaced at least about 30°, at least 40°, at least 50°, or at least 55° apart from the first row of gas outlet openings around the circumference of the gas delivery device, when viewed in cross-section (and/or, in some embodiments, less than about 90°, less than about 80°, less than about 70°, or less than about 65° apart from the first row of gas outlet openings around the circumference of the gas delivery device, when viewed in cross-section). In certain embodiments, there are no rows of gas outlet openings between the first and second rows of gas outlet openings. In some embodiments, there are no rows of gas outlet openings between the first and third rows of gas outlet openings. As one example, referring to FIG. 6D, in one set of embodiments, a first row of gas outlet openings can be located at position 652 (and extend into and out of the page), a second row of gas outlet openings can be located at position 654 (and extend into and out of the page), and a third row of gas outlet openings can be located at position 655 (and extend into and out of the page). In some such embodiments, and as illustrated in FIG. 6D, the first row of gas outlet openings can face upward during operation of the gas delivery device.

Additional rows of gas outlet openings may also be present. For example, in some embodiments, the gas delivery portion includes a fourth row of gas outlet openings extending in a direction along a longitudinal axis of the primary conduit. In some embodiments, the fourth row of gas outlet openings and the second row of gas outlet openings are spaced at least about 30°, at least 40°, at least 50°, or at least 55° apart from each other around the circumference of the gas delivery device, when viewed in cross-section (and/or, in some embodiments, less than about 90°, less than about 80°, less than about 70°, or less than about 65° apart from each other around the circumference of the gas delivery device, when viewed in cross-section). The fourth row of gas outlet openings can be on the opposite side of the second row of gas outlet openings as the first row of gas outlet openings, in some embodiments. For example, referring to FIG. 6D, in some embodiments, a fourth row of gas outlet openings can be located at position 656 (and extend into and out of the page). In certain embodiments, there are no rows of gas outlet openings between the second and fourth rows of gas outlet openings.

In some embodiments, the gas delivery portion includes a fifth row of gas outlet openings extending in a direction along a longitudinal axis of the primary conduit. In some embodiments, the fifth row of gas outlet openings and the third row of gas outlet openings are spaced at least about 30°, at least 40°, at least 50°, or at least 55° apart from each other around the circumference of the gas delivery device, when viewed in cross-section (and/or, in some embodiments, less than about 90°, less than about 80°, less than about 70°, or less than about 65° apart from each other around the circumference of the gas delivery device, when viewed in cross-section). The fifth row of gas outlet openings can be on the opposite side of the third row of gas outlet openings as the first row of gas outlet openings, in some embodiments. For example, referring to FIG. 6D, in some embodiments, a fifth row of gas outlet openings can be located at position 657 (and extend into and out of the page). In certain embodiments, there are no rows of gas outlet openings between the third and fifth rows of gas outlet openings.

In some embodiments, the gas delivery portion includes a sixth row of gas outlet openings extending in a direction along a longitudinal axis of the primary conduit. In some embodiments, the sixth row of gas outlet openings and the first row of gas outlet openings are spaced at least about 150°, at least 160°, at least 170°, or at least 175° apart from each other around the circumference of the gas delivery device, when viewed in cross-section. For example, referring to FIG. 6D, in some embodiments, a sixth row of gas outlet openings can be located at position 650 (and extend into and out of the page).

According to certain embodiments, during use, the average linear velocity of gas exiting the gas outlet openings of a conduit of the gas for advice can be at least about 0.1 m/s, at least about 0.2 m/s, at least about 0.5 m/s, at least about 1 m/s, at least about 2 m/s, at least about 5 m/s, at least about 8 m/s, or more (and/or, in some embodiments, less than about 80 m/s, less than about 70 m/s, less than about 60 m/s, less than about 50 m/s, less than about 40 m/s, less than about 30 m/s, less than about 20 m/s, or less than about 15 m/s). It should be understood that the ranges recited above can be employed alone or in any combination of a lower bound range and an upper bound range. For example, in one set of embodiments, during use, the average linear velocity of gas exiting the gas outlet openings of a conduit of the gas for advice can be at least about 0.1 m/s. In one set of embodiments, during use, the average linear velocity of gas exiting the gas outlet openings of a conduit of the gas for advice can be at least about 8 m/s. In one set of embodiments, during use, the average linear velocity of gas exiting the gas outlet openings of a conduit of the gas for advice can be less than about 80 m/s. In one set of embodiments, during use, the average linear velocity of gas exiting the gas outlet openings of a conduit of the gas for advice can be less than about 30 m/s. In one set of embodiments, during use, the average linear velocity of gas exiting the gas outlet openings of a conduit of the gas for advice can be less than about 15 m/s. In one set of embodiments, during use, the average linear velocity of gas exiting the gas outlet openings of a conduit of the gas for advice can be at least about 8 m/s and less than about 15 m/s.

All average values described herein are calculated as mathematical means (see, e.g., Equation [2] above), unless otherwise specified.

The following examples are intended to illustrate certain embodiments of the present invention, but do not exemplify the full scope of the invention.

Example 1

This example describes experiments in which a gas delivery device was used to deliver gas bubbles to a liquid medium. The system included a rectangular polyethylene glass container filled with water and having an internal cavity with a height of 1220.0 mm, a width of 500.0 mm, and a depth of 25.4 mm. A gas delivery device, including a cylindrical secondary conduit nested within a cylindrical primary conduit, was arranged at the bottom of the container. The primary conduit was a plastic tube, approximately 380.0 mm long, with an internal diameter of 6.4 mm. The primary conduit included 7 gas outlet openings spaced 10.0 mm apart. The secondary conduit was a stainless steel tube, approximately 240.0 mm long, with an external diameter of 3.2 mm and an internal diameter of 2.2 mm. The secondary conduit included 5 gas outlet openings spaced 5.0 mm apart. The primary and secondary conduits were arranged as illustrated in FIGS. 1A-1B.

A data acquisition system was incorporated into the system to determine the gas velocity exiting the gas outlet openings of the primary conduit and bubble size. The data acquisition system included a LabView DAQ system, a mass flow controller, four sets of differential pressure transducers, and a high speed camera (HSC, Fastcam SA3). Data was analyzed using ProAnalyze software.

Compressed air was transported through the inlet end of the primary conduit at volumetric flow rates of 0.2-20.0 L/min, and air bubbles were ejected from the gas outlet openings of the primary conduit.

Figure 7A:
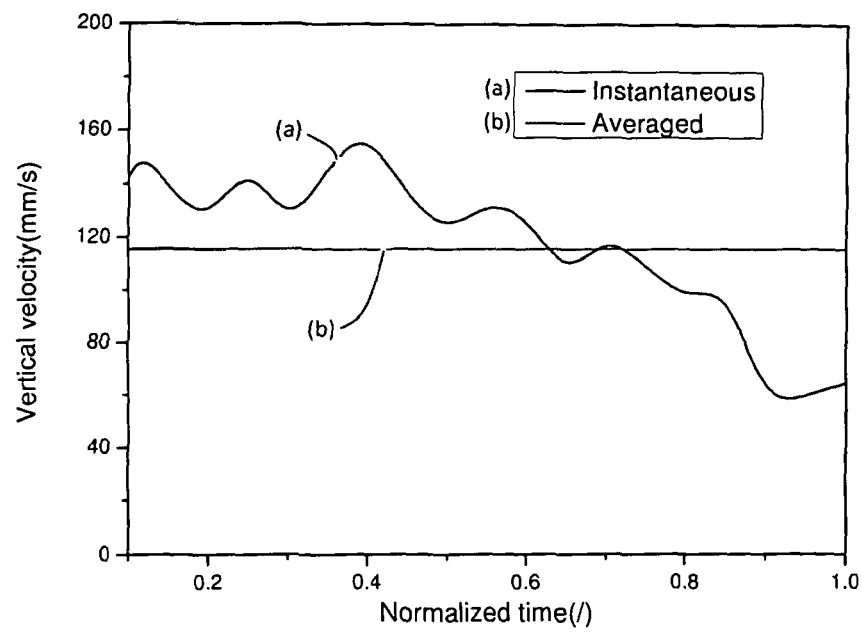
FIGS. 7A-7D are plots of experimentally determined linear gas flow velocities from the gas outlet openings of a primary conduit, as a function of time, according to one set of embodiments.
Figure 7B:
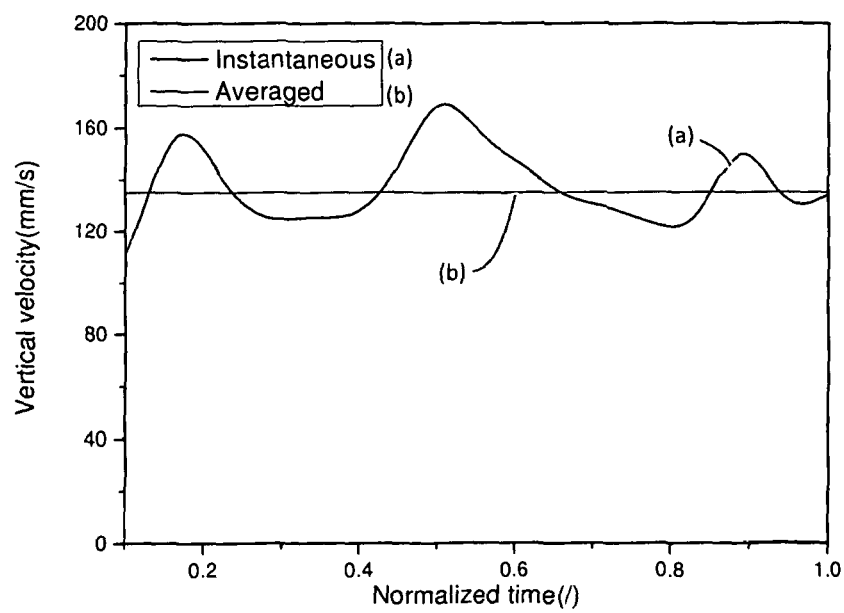
Figure 7C:
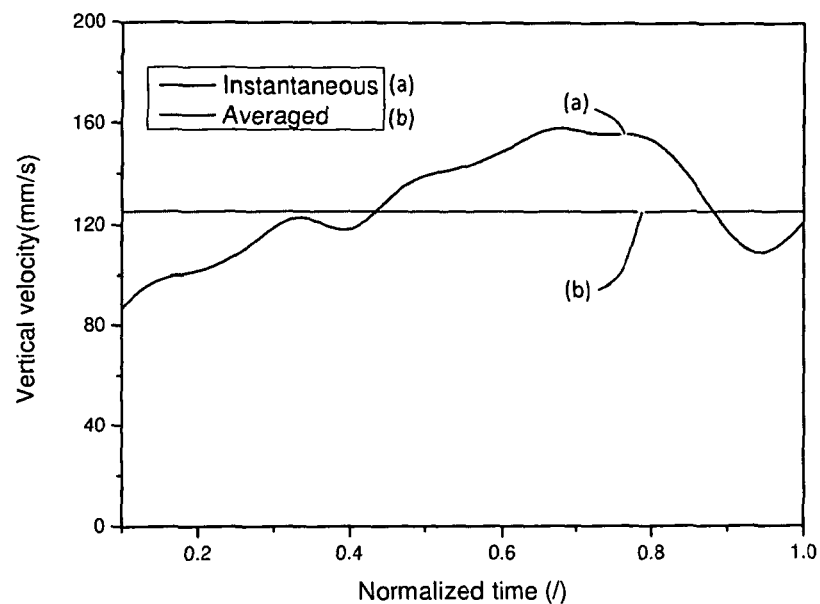
Figure 7D:
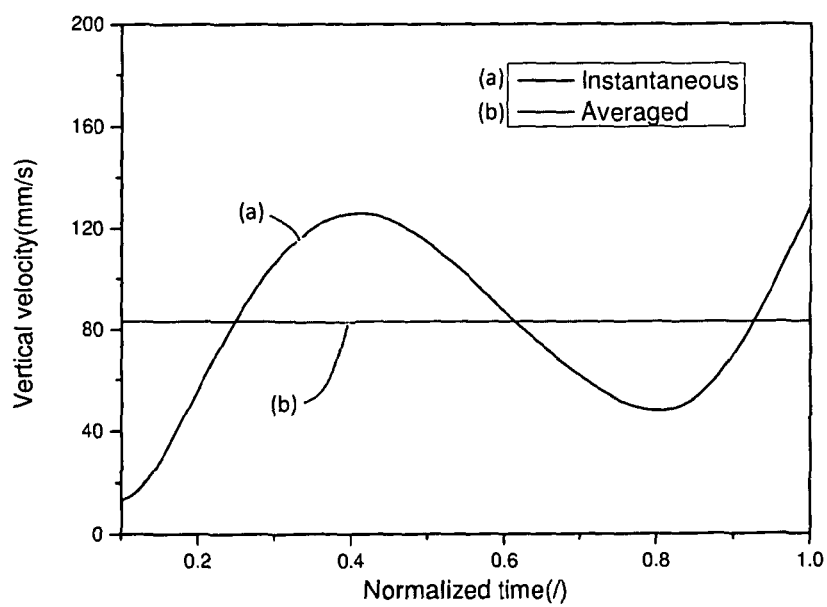

In a first set of experiments, the secondary conduit was left in place within the primary conduit. FIGS. 7A and 7B are plots of the instantaneous and averaged linear gas flow velocities as a function of time for the gas outlet opening in the primary conduit nearest the entrance and the gas outlet opening farthest from the entrance, respectively. A second set of experiments were performed in which the secondary conduit was removed from the primary conduit. FIGS. 7C and 7D are plots of the instantaneous and averaged linear gas flow velocities as a function of time for the gas outlet opening in the primary conduit nearest the entrance and the gas outlet opening farthest from the entrance, respectively, when the secondary conduit was removed. As shown in FIGS. 7A-7D, the average velocities of the gas exiting the two gas outlet openings when the secondary conduit was in place were much closer (118 mm/s vs. 138 mm/s) than when the secondary conduit was removed (82 mm/s vs. 125 mm/s).

Example 2

This example describes the results of theoretical simulations in which a gas delivery device was used to deliver air bubbles to water.

In the simulated system, the liquid medium was assumed to have a volume of 10 L. The gas delivery device was modeled as including a cylindrical secondary conduit nested within a cylindrical primary conduit. In the simulations, the primary and secondary conduits were arranged as illustrated in FIGS. 1A-1B.

To determine the velocity at each gas outlet opening, the equations outlined in Table 1 were used. In these equations, v is the linear gas velocity, c is the orifice discharge coefficient (assumed to be 0.92), p is the gas pressure, $\rho_g$ is the gas density, $\lambda$ is the friction factor, Re is the Reynolds number, L is the length of the primary conduit, and $d_L$ is the hydraulic diameter of the primary conduit (in this case, the internal diameter of the primary conduit). The momentum recovery coefficient was assumed to be 0.5, as noted in Equation E4 in Table 1.

TABLE 1

| Equations used to perform simulation in Example 2 | |
| --- | --- |
| [E1] Velocity Correction | $v_i = c\sqrt{(p_i - p_a)/g}$ |
| [E2] Colebrook equation | $\frac{1}{\sqrt{\lambda}} = -2\log[2.51/(Re\lambda^{0.5})]$ |
| [E3] Momentum balance (horizontal) | $\rho_g v^2 + p = \text{constant}$ |
| [E4] Darcy-Weisbach equation | $\Delta p = \lambda(L/d_L)(0.5\rho_g v^2)$ |
| [E5] Mass conservation equation | $\dot{m} = \sum_{i=1}^{n} m_i$ |

To calculate the linear gas flow velocity at each gas outlet opening, the following procedure was used:
(1) The initial mass flux and nozzle velocity for each of n nozzles i=1, 2, . . . n) was set.
(2) Next, the pressure at the first gas outlet opening was calculated using Equation E1 in Table 1, and the Reynolds number and friction factor was calculated using Equation E2 in Table 1.

(3) Next, the pressure loss and momentum recovery were calculated using Equations E3 and E4 in Table 1.

(4) The pressure distribution and corrected velocity were then calculated for the (i+1) opening, using Equation E1.

(5) If the difference between the inlet mass flux and the sum of the gas outlet opening mass fluxes was less than a fixed tolerance level, the solution was output.

(6) If the difference between the inlet mass flux and the sum of the gas outlet opening mass fluxes was greater than the fixed tolerance level, m(i) was set to the inlet mass flux divided by the sum of the mass fluxes out of the gas outlet openings, and the process outlined above was repeated, beginning with Step 3. This process was repeated until the difference between the inlet mass flux and the sum of the gas outlet opening mass fluxes was less than the fixed tolerance level.

Figure 8A:
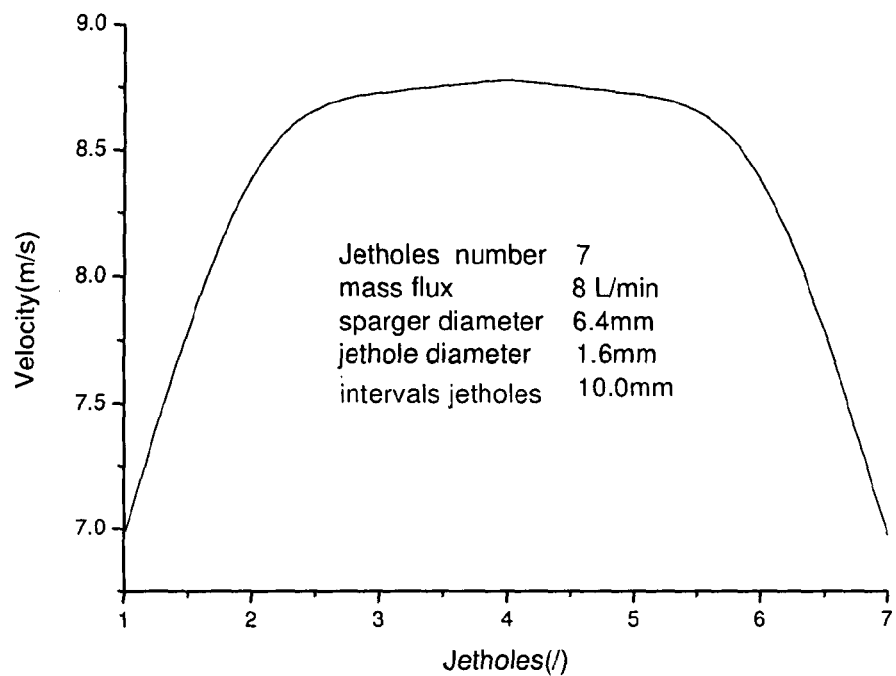
FIGS. 8A-8D are, according to certain embodiments, plots of simulated linear gas flow velocities from the gas outlet openings of a primary conduit (including 7 gas outlet openings), as a function of the index number of each gas outlet opening, according to one set of embodiments.
Figure 8B:
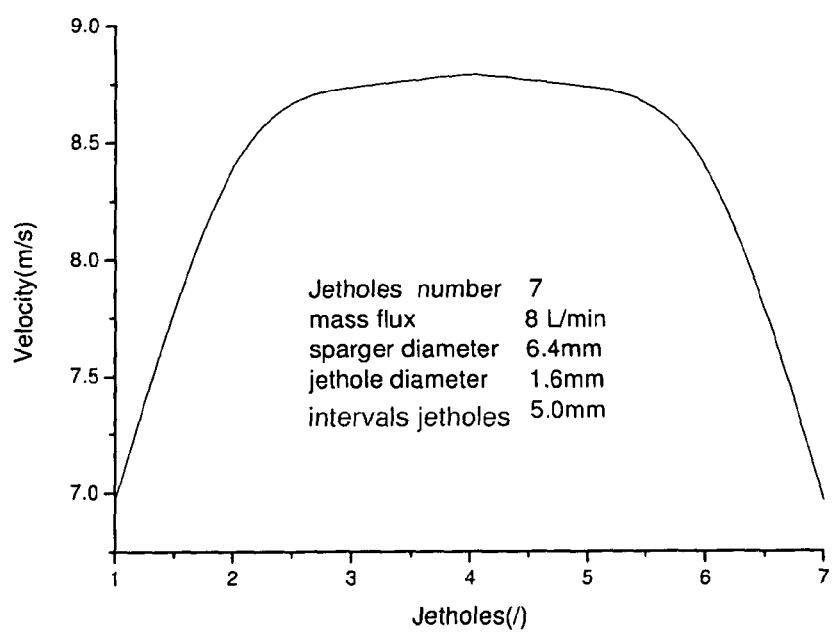
Figure 8C:
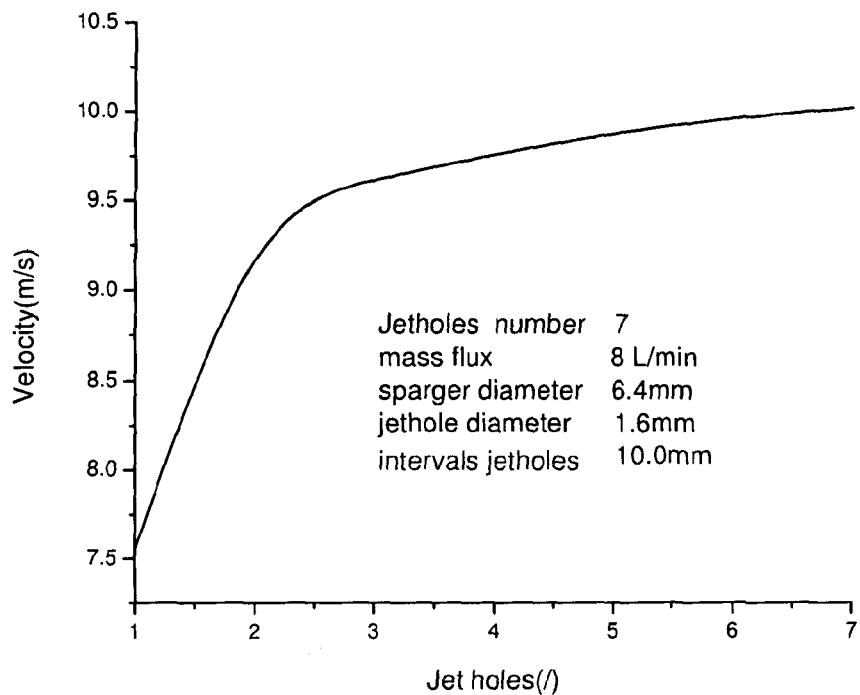
Figure 8D:
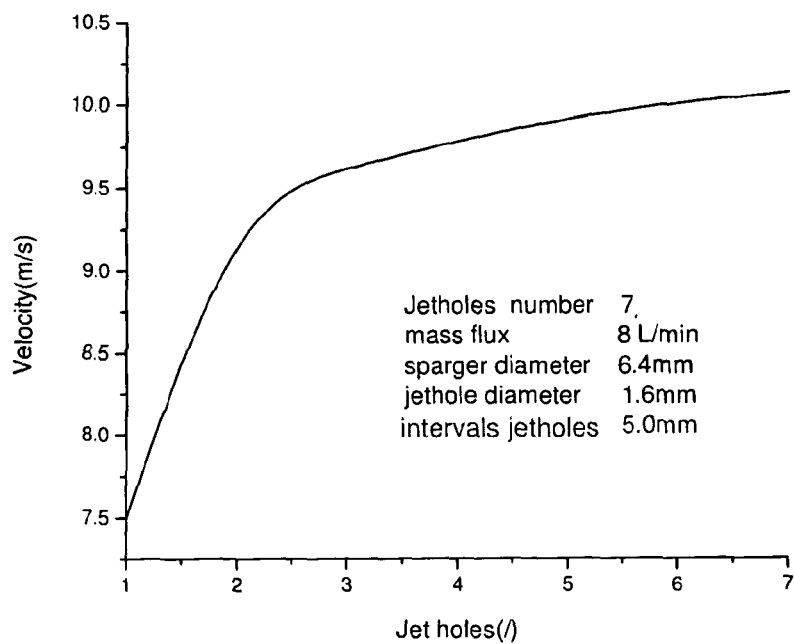

In a first set of simulations, a primary conduit including 7 gas outlet openings was modeled. The primary conduit had an internal diameter of 6.4 mm, and included 1.6 mm gas outlet openings. In a first set of simulations, the gas outlet openings were spaced 10.0 mm apart, and in a second set of simulations, the gas outlet openings were spaced 5.0 mm apart. The secondary conduit was modeled to include 5 gas outlet openings spaced 5.0 mm apart. The secondary conduit had an external diameter of 3.2 mm and an internal diameter of 2.2 mm. The linear velocities of the gas exiting from each of the gas outlet openings were determined with and without the secondary conduit in place. The results of these simulations are shown in FIGS. 8A-8D. FIGS. 8A-8B show the gas flow distributions when the secondary conduit was in place, while FIGS. 8C-8D show the gas flow distributions when the secondary conduit was removed. The x-axes in FIGS. 8A-8D include the index numbers of the evenly-spaced gas outlet openings of the primary conduit (with i=1 corresponding to the opening closest to the gas inlet of the primary conduit and i=7 corresponding to the opening farthest from the gas inlet of the primary conduit). Thus, the x-axes in FIGS. 8A-8D are indicative of position along the length of the primary conduit. When the secondary conduit was in place, the differences between the minimum and maximum linear gas flow velocities were substantially smaller than the differences when the secondary conduit was removed, as summarized in Table 1 below.

TABLE 1

Simulation results for gas delivery device with 7 gas outlet openings

| Secondary Conduit in Place? | Gas Outlet Opening Spacing | Min. linear gas velocity (m/s) | Max. linear gas velocity (m/s) |
|---|---|---|---|
| Yes | 10.0 mm | 6.9 | 8.8 |
| Yes | 5.0 mm | 6.9 | 8.7 |
| No | 10.0 mm | 7.5 | 10.0 |
| No | 5.0 mm | 7.4 | 10.1 |

Figure 9A:
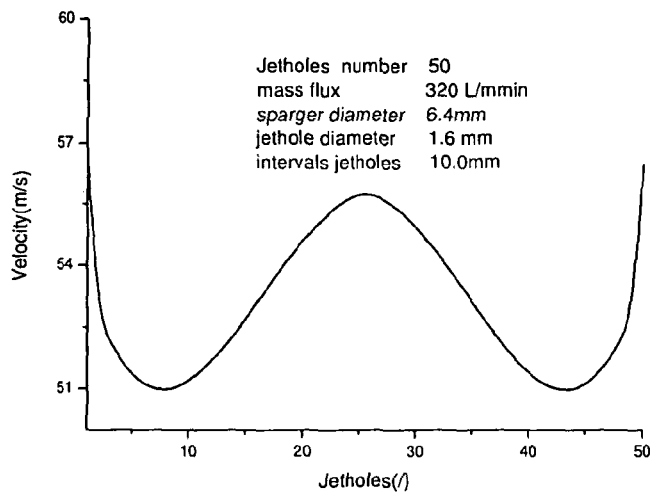
FIGS. 9A-9F are plots of simulated linear gas flow velocities from the gas outlet openings of a primary conduit (including 50 gas outlet openings), as a function of the index number of each gas outlet opening, according to one set of embodiments.
Figure 9B:
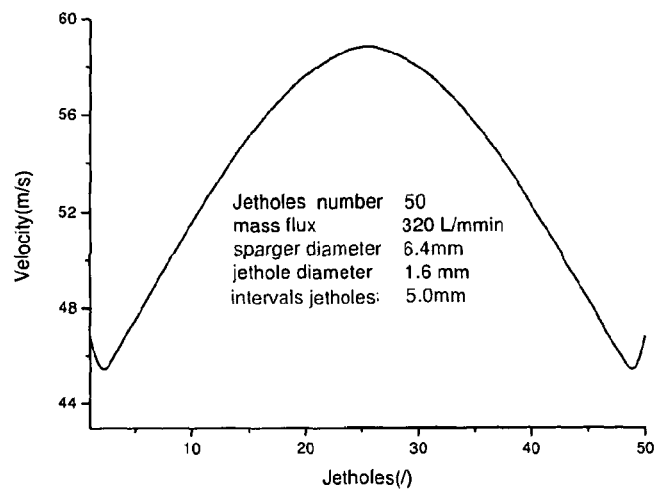
Figure 9C:
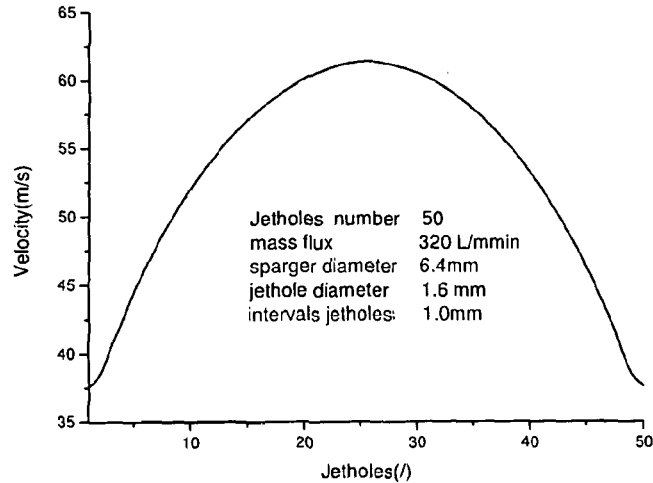
Figure 9D:
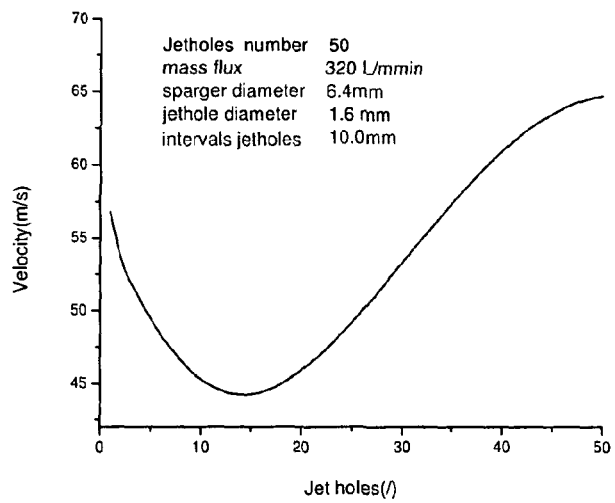
Figure 9E:
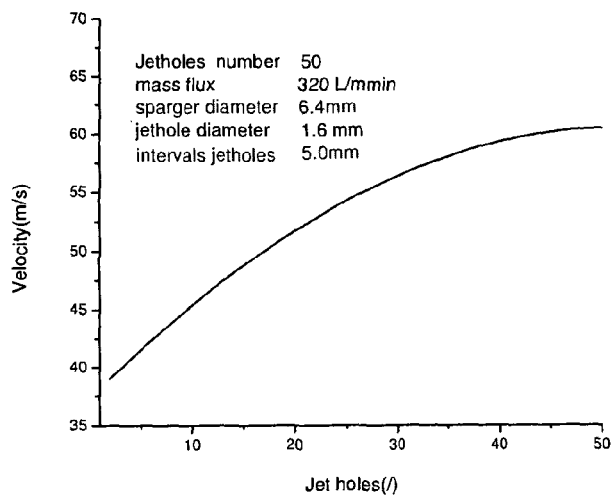
Figure 9F:
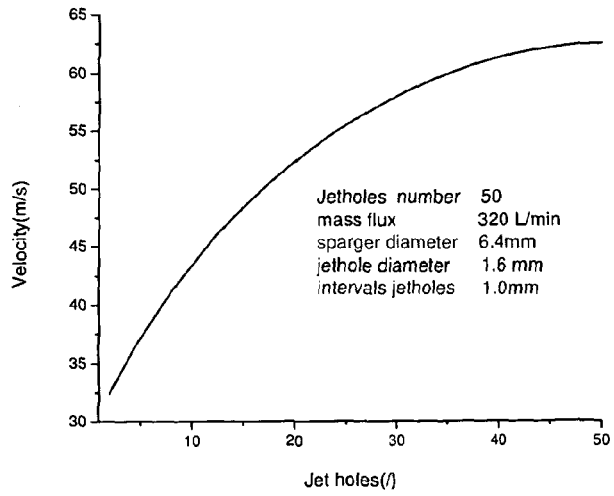

In a second set of simulations, a primary conduit including 50 gas outlet openings was modeled. The primary conduit had an internal diameter of 6.4 mm, and included 1.6 mm gas outlet openings. The gas outlet openings were spaced 10.0 mm apart in a first set of simulations, 5.0 mm apart in a second set of simulations, and 1.0 mm apart in a third set of simulations. The secondary conduit was modeled to include 5 gas outlet openings spaced 5.0 mm apart. The secondary conduit had an external diameter of 3.2 mm and an internal diameter of 2.2 mm. The linear velocities of the gas exiting from each of the gas outlet openings were determined with and without the secondary conduit in place. The results of these simulations are shown in FIGS. 9A-9F. FIGS. 9A-9C show the gas flow distributions when the secondary conduit was in place, while FIGS. 9D-9F show the gas flow distributions when the secondary conduit was removed. The x-axes in FIGS. 9A-9F include the index numbers of the evenly-spaced gas outlet openings of the primary conduit (with i=1 corresponding to the opening closest to the gas inlet of the primary conduit and i=50 corresponding to the opening farthest from the gas inlet of the primary conduit). Thus, the x-axes in FIGS. 9A-9F are indicative of position along the length of the primary conduit. When the secondary conduit was in place, the differences between the minimum and maximum linear gas flow velocities were substantially smaller than the differences present when the secondary conduit was removed, as summarized in Table 2 below.

TABLE 2

Simulation results for gas delivery device with 50 gas outlet openings.

| Secondary Conduit in Place? | Gas Outlet Opening Spacing | Min. linear gas velocity (m/s) | Max. linear gas velocity (m/s) |
|---|---|---|---|
| Yes | 10.0 mm | 51.0 | 55.8 |
| Yes | 5.0 mm | 45.0 | 58.9 |
| Yes | 1.0 mm | 37.6 | 61.5 |
| No | 10.0 mm | 44.2 | 64.8 |
| No | 5.0 mm | 38.9 | 60.5 |
| No | 1.0 mm | 32.4 | 62.5 |

Example 3

This example describes experiments in which the angle of the gas delivery device was varied within a bioreactor to determine the impact of adjusting the alignment of gas outlet openings on bubble production.

Figure 10A:
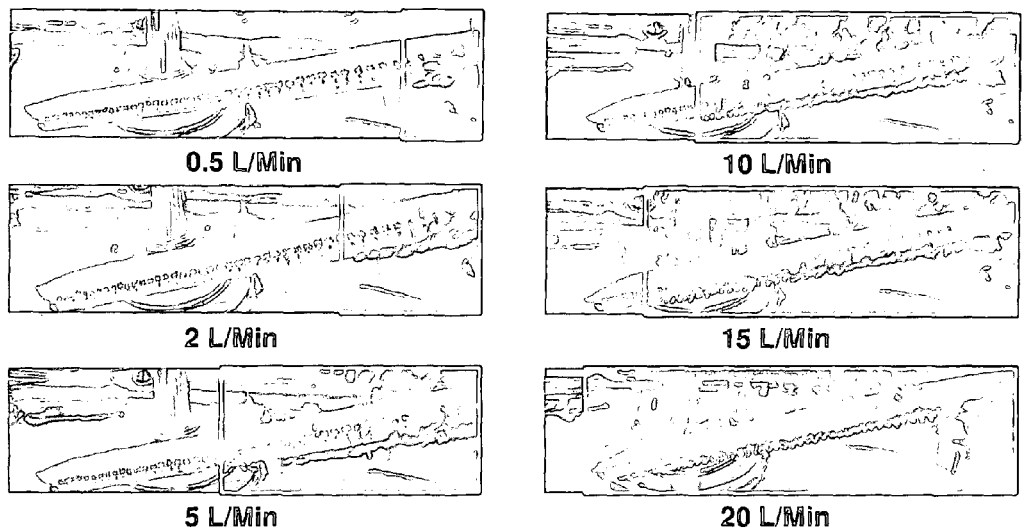
FIGS. 10A-10B are photographs of gas delivery devices, illustrating the impact of orienting the openings of the devices in a horizontal configuration, according to certain embodiments.
Figure 10B:
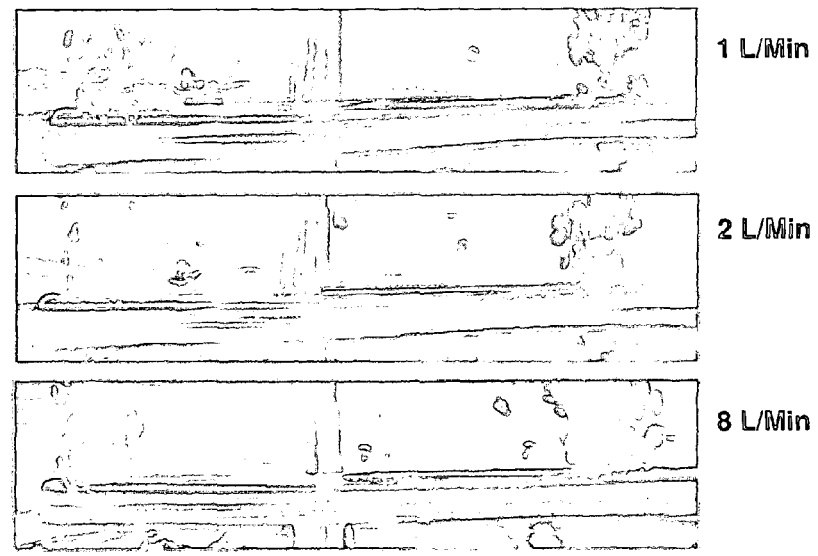

In a first set of experiments, gas was introduced to a 200 L bioreactor filled with water using a gas delivery device oriented at a 15° angle, as illustrated in FIG. 10 A. As shown in FIG. 10 A, bubbles were not generated across the entire gas delivery device until an average linear flow rate of 20 L/minute was reached. Such high flow rates can damage cells, reducing product output from the bioreactor.

In a second set of experiments, the gas outlet openings of the gas delivery device were arranged substantially horizontally. As shown in FIG. 10 B, bubbles were generated from all gas outlet openings at flow rates as low as 1 L/minute, 20 times smaller than the flow rates required to generate even bubble distribution from the angled gas delivery device.

Example 4

This example describes experiments in which gas outlet opening spacings and gas outlet opening orientations were varied to determine the impact on cell growth in a bioreactor.

Two different gas delivery devices were used in a bioreactor to grow CHO cells.

A first set of experiments was performed using a first gas delivery device (D1). Gas delivery device D1 was inserted into the bioreactor at a 15° downward grade. Gas delivery device D1 included 12 cylindrical gas outlet openings, each having cross-sectional diameters of 0.5 mm spaced 2.5 mm apart.

A second set of experiments was performed using a second gas delivery device (D2), which was oriented horizontally in the bioreactor, and which included 65 cylindrical holes having cross-sectional diameters of 0.5 mm spaced 3.5 mm apart.

Figure 11:
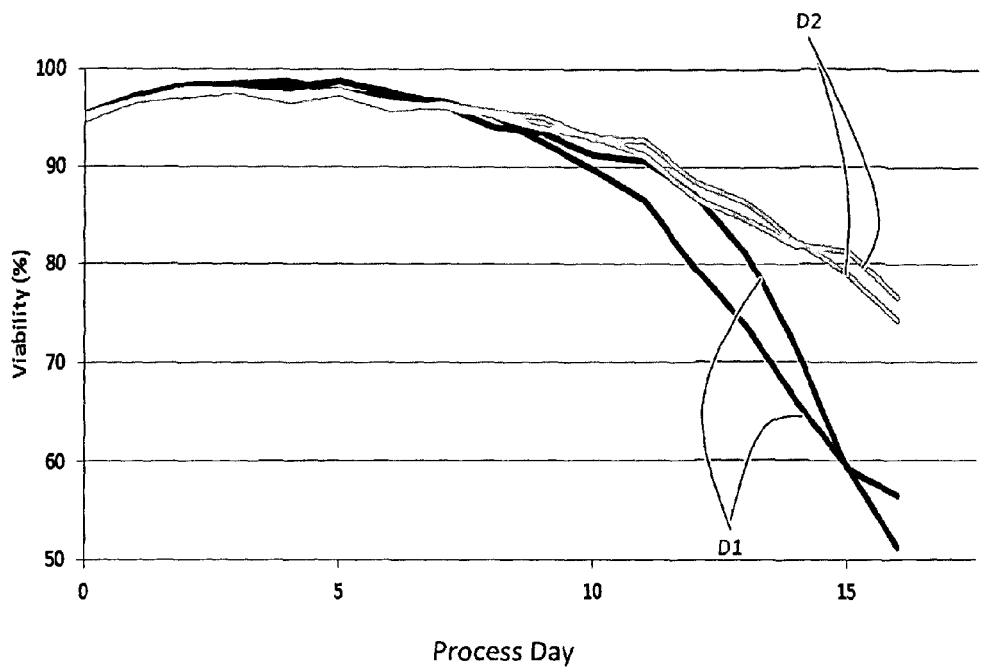
FIG. 11 is a plot of cell viability as a function of time for the experiments described in Example 4.

FIG. 11 is a plot of cell viability as a function of time for four experiments run using gas delivery devices D1 and D2. As shown in FIG. 11, the long-term cell viability was 20% greater in experimental runs in which horizontally positioned gas delivery devices were employed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for producing bubbles of a gas within a liquid, comprising:
   a primary conduit comprising a plurality of openings fluidically connecting an internal flow pathway of the primary conduit to an environment outside the primary conduit; and
   a secondary conduit located at least partially within the primary conduit, the secondary conduit configured to redistribute the pressure of the gas delivered to the openings of the primary conduit, and comprising a plurality of openings fluidically connecting an internal flow pathway of the secondary conduit to a portion of the internal flow pathway of the primary conduit outside the secondary conduit,
   wherein the primary conduit comprises a gas inlet opening at or near an end of the primary conduit.

2. The device of claim 1, wherein a longitudinal axis of the primary conduit is substantially parallel to a longitudinal axis of the secondary conduit.

3. The device of claim 1, wherein the primary conduit does not include a second gas inlet opening.

4. The device of claim 1, wherein the primary conduit comprises a plurality of gas outlet openings in a wall of the primary conduit.

5. The device of claim 4, wherein the primary conduit comprises at least three gas outlet openings in the wall of the primary conduit.

6. The device of claim 4, wherein the gas outlet openings of the primary conduit have a cross-sectional shape that tapers in size along the length of a longitudinal axis of the gas outlet openings.

7. The device of claim 4, wherein longitudinal axes of the gas outlet openings of the primary conduit are substantially parallel.

8. The device of claim 1, wherein the gas outlet openings of the primary conduit are part of a porous medium making up a portion of the wall of the primary conduit.

9. The device of claim 1, wherein the secondary conduit comprises a gas inlet opening at or near an end of the secondary conduit.

10. The device of claim 1, wherein the secondary conduit comprises a plurality of gas outlet openings in a wall of the secondary conduit.

11. The device of claim 10, wherein the secondary conduit comprises at least three gas outlet openings in the wall of the secondary conduit.

12. The device of claim 1, wherein the secondary conduit has a substantially circular cross-sectional shape.

13. The device of claim 1, wherein the primary conduit has a substantially circular cross-sectional shape.

14. The device of claim 1, wherein the secondary conduit is defined by at least one partition separating an interior portion of the secondary conduit from an interior portion of the primary conduit.

15. The device of claim 1, wherein the device is part of a bioreactor.

16. The device of claim 1, wherein:
an average of cross-sectional diameters of the openings of the primary conduit is less than about 2.5 mm, and
an average of nearest neighbor distances between the openings of the primary conduit is at least about 2 mm.

17. A device for producing bubbles of a gas within a liquid, comprising:
a primary conduit comprising a plurality of gas outlet openings in a wall of the primary conduit, the gas outlet openings fluidically connecting an internal flow pathway of the primary conduit to an environment outside the primary conduit; and
a secondary conduit located at least partially within the primary conduit, the secondary conduit configured to redistribute the pressure of the gas delivered to the gas outlet openings of the primary conduit, and comprising a plurality of openings fluidically connecting an internal flow pathway of the secondary conduit to a portion of the internal flow pathway of the primary conduit outside the secondary conduit,
wherein the gas outlet openings of the primary conduit have a cross-sectional shape that tapers in size along lengths of longitudinal axes of the gas outlet openings.

18. A device for producing bubbles of a gas within a liquid, comprising:
a primary conduit comprising a plurality of gas outlet openings in a wall of the primary conduit, the gas outlet openings fluidically connecting an internal flow pathway of the primary conduit to an environment outside the primary conduit; and
a secondary conduit located at least partially within the primary conduit, the secondary conduit configured to redistribute the pressure of the gas delivered to the gas outlet openings of the primary conduit, and comprising a plurality of openings fluidically connecting an internal flow pathway of the secondary conduit to a portion of the internal flow pathway of the primary conduit outside the secondary conduit,
wherein longitudinal axes of the gas outlet openings of the primary conduit are substantially parallel.

19. A device for producing bubbles of a gas within a liquid, comprising:
a primary conduit comprising a plurality of gas outlet openings in a wall of the primary conduit, the gas outlet openings fluidically connecting an internal flow pathway of the primary conduit to an environment outside the primary conduit; and
a secondary conduit located at least partially within the primary conduit, the secondary conduit configured to redistribute the pressure of the gas delivered to the gas outlet openings of the primary conduit, and comprising a plurality of openings fluidically connecting an internal flow pathway of the secondary conduit to a portion of the internal flow pathway of the primary conduit outside the secondary conduit,
wherein the gas outlet openings of the primary conduit are part of a porous medium making up a portion of the wall of the primary conduit.

20. A device for producing bubbles of a gas within a liquid, comprising:
a primary conduit comprising a plurality of openings fluidically connecting an internal flow pathway of the primary conduit to an environment outside the primary conduit; and
a secondary conduit located at least partially within the primary conduit, the secondary conduit configured to redistribute the pressure of the gas delivered to the openings of the primary conduit, and comprising a plurality of openings fluidically connecting an internal flow pathway of the secondary conduit to a portion of the internal flow pathway of the primary conduit outside the secondary conduit,
wherein the secondary conduit is defined by at least one partition separating an interior portion of the secondary conduit from an interior portion of the primary conduit.

* * * * *